US008187217B2

(12) United States Patent
Renati et al.

(10) Patent No.: US 8,187,217 B2
(45) Date of Patent: *May 29, 2012

(54) TMR SHUNT

(76) Inventors: Richard J. Renati, Los Gatos, CA (US);
Mark A. Bowen, Stow, MA (US);
Stephen C. Evans, Westford, MA (US);
Margaret G. McCabe, Pleasant Hill, CA (US); Marvin Guiles, Stow, MA (US); Fernando Alvarez de Toledo, Concord, MA (US); Gerald Melsky, Lexington, MA (US)

( * ) Notice: Subject to any disclaimer, the term of this patent is extended or adjusted under 35 U.S.C. 154(b) by 1492 days.

This patent is subject to a terminal disclaimer.

(21) Appl. No.: 11/155,628

(22) Filed: Jun. 20, 2005

(65) Prior Publication Data
US 2006/0116625 A1    Jun. 1, 2006

Related U.S. Application Data

(63) Continuation of application No. 09/956,099, filed on Sep. 20, 2001, now Pat. No. 6,926,690, which is a continuation of application No. 09/787,801, filed as application No. PCT/US99/20714 on Sep. 10, 1999, now abandoned.

(60) Provisional application No. 60/099,767, filed on Sep. 10, 1998, provisional application No. 60/104,397, filed on Oct. 15, 1998, provisional application No. 60/147,202, filed on Aug. 4, 1999, provisional application No. 60/147,218, filed on Aug. 4, 1999.

(51) Int. Cl.
*A61M 5/00* (2006.01)

(52) U.S. Cl. ................................. 604/8; 604/9; 604/10
(58) Field of Classification Search ............... 604/7–10, 604/264, 266, 526, 527, 530, 532; 623/1.1, 623/1.12, 1.14, 1.15, 1.2, 1.31, 1.39, 1.42, 623/1.45, 1.46, 1.3; 606/153, 194, 108, 167, 606/170
See application file for complete search history.

(56) References Cited

U.S. PATENT DOCUMENTS

| | | | | |
|---|---|---|---|---|
| 4,230,119 | A * | 10/1980 | Blum | 606/194 |
| 5,755,682 | A * | 5/1998 | Knudson et al. | 604/8 |
| 5,868,697 | A * | 2/1999 | Richter et al. | 604/8 |
| 6,124,523 | A * | 9/2000 | Banas et al. | 623/1.15 |
| 6,293,955 | B1 * | 9/2001 | Houser et al. | 606/153 |
| 6,406,488 | B1 * | 6/2002 | Tweden et al. | 623/1.16 |
| 6,692,520 | B1 * | 2/2004 | Gambale et al. | 623/1.1 |
| 6,926,690 | B2 * | 8/2005 | Renati | 604/8 |

* cited by examiner

*Primary Examiner* — Leslie Deak

(57) ABSTRACT

A conduit is provided to provide a bypass around a blockage in the coronary artery. The conduit is adapted to be positioned in the myocardium or heart wall to provide a passage for blood to flow between a chamber of the heart such as the left ventricle and the coronary artery, distal to the blockage. The stent is self-expanding or uses a balloon to expand the stent in the heart wall. Various attachment means are provided to anchor the stent and prevent its migration. In one embodiment, a conduit is provided having a distal top which is more preferably a ball top, wire top, flare top or flip-down top. These top configurations anchor the shunt at one end in the coronary artery.

19 Claims, 55 Drawing Sheets

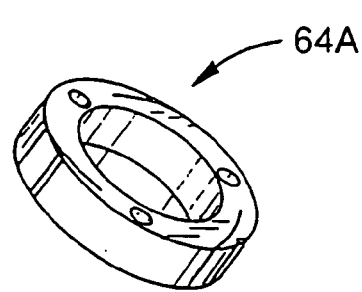
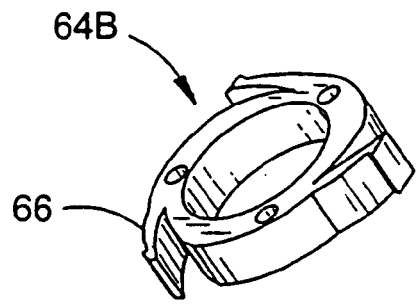
FIG. 22  FIG. 23
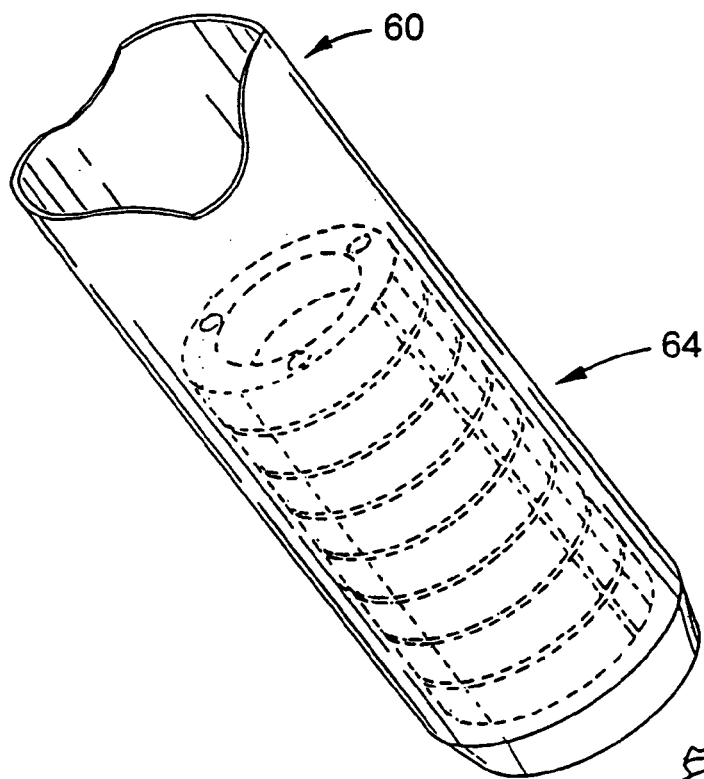
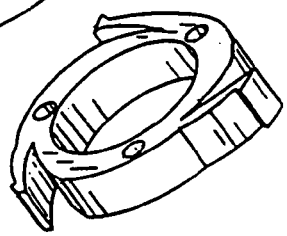
FIG. 24

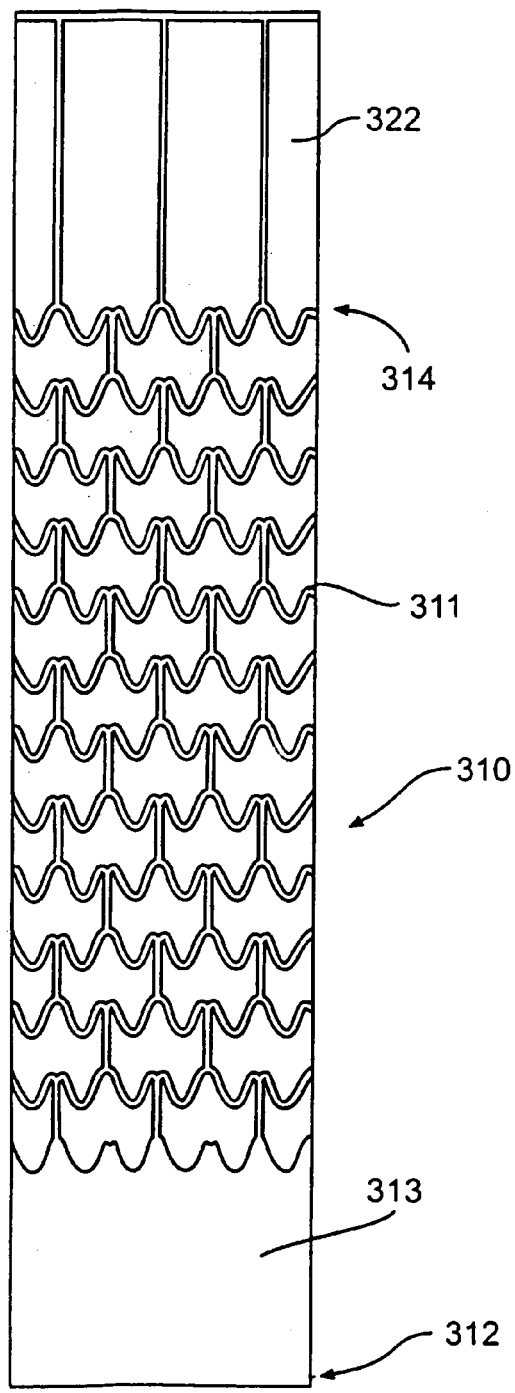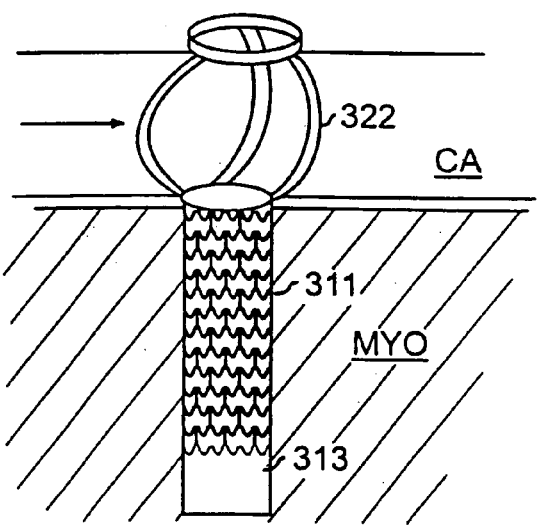
FIG. 34F
FIG. 34G

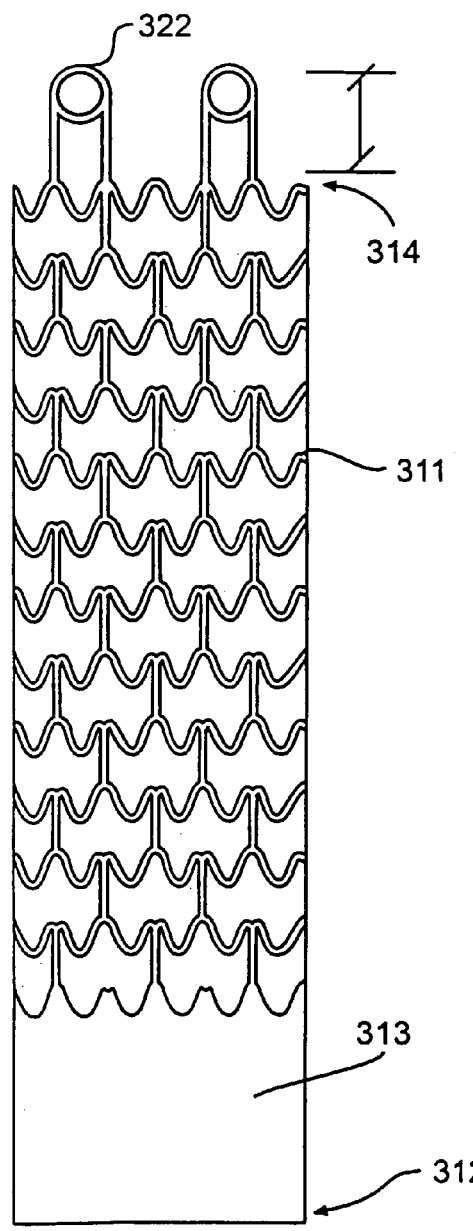
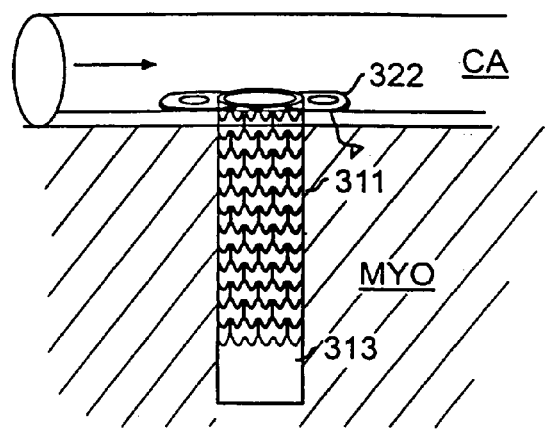
FIG. 40B
FIG. 40C

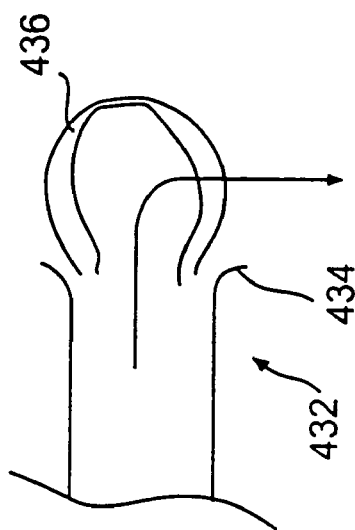
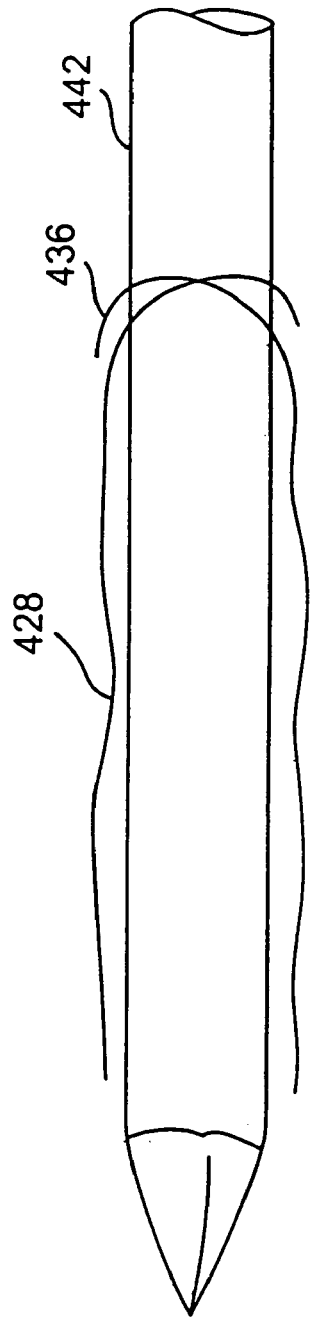
FIG. 44B
FIG. 44C

TMR SHUNT

CROSS-REFERENCE TO RELATED APPLICATIONS

This application is a continuation of U.S. patent application Ser. No. 09/956,099 filed Sep. 20, 2001 now U.S. Pat. No. 6,926,690, which is a continuation of U.S. patent application Ser. No. 09/787,801, now abandoned, which is a national stage entry of PCT/US99/20714 filed Sep. 10, 1999, now abandoned, which claims priority to U.S. patent application Ser. No. 09/369,048 filed Aug. 4, 1999, now abandoned, U.S. Provisional Patent Application No. 60/147,202 filed Aug. 4, 1999, U.S. Provisional Patent Application No. 60/147,218 filed Aug. 4, 1999, U.S. Provisional Patent Application No. 60/104,397 filed Oct. 15, 1998, and U.S. Provisional Patent Application No. 60/099,767 filed Sep. 10, 1998, the entirety of all of which are incorporated herein by reference.

FIELD OF THE INVENTION

The present invention relates to an apparatus for bypassing a blocked blood vessel segment, and, more particularly, to a conduit or stent positioned between the coronary artery or other blocked vessel and a chamber of the heart, such as the left ventricle of the heart, to bypass a blocked segment of the coronary artery or other blood vessel.

BACKGROUND OF THE INVENTION

Coronary artery disease is a major problem in the U.S. and throughout the world. Coronary arteries as well as other blood vessels frequently become clogged with plaque, which at the very least impairs the efficiency of the heart's pumping action, and can lead to heart attack and death. In some cases, these arteries can be unblocked through non-invasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A vein graft is harvested from the patient's leg, another highly invasive procedure, and a delicate surgical procedure is required to piece the bypass graft to the coronary artery (anastomosis). Hospital stays subsequent to the surgery and convalescence are prolonged.

As mentioned above, another conventional treatment is percutaneous transluminal coronary angioplasty (PTCA) or other types of angioplasty. However, such vascular treatments are not always indicated due to the type or location of the blockage, or due to the risk of emboli.

Thus, there is a need for an improved bypass system which is less traumatic to the patient.

SUMMARY OF THE INVENTION

The preferred embodiments of the present invention address the need in the previous technology by providing a bypass system that avoids the sternotomy and other intrusive procedures normally associated with coronary bypass surgery. These embodiments also free the surgeon from the multiple anastomoses necessary in the current process.

The preferred device provides a shunt for diverting blood directly from a chamber in the heart, such as the left ventricle, to the coronary artery, distal to the blockage, therefore bypassing the blocked portion of the vessel. The shunt comprises a stent or conduit adapted to be positioned in the heart wall or myocardium between a chamber in the heart such as the left ventricle and the coronary artery that allows for the direct passage of blood therethrough. As used herein, the terms "stent" and "conduit" are interchangeable, and refer to a device that allows for the passage of blood therethrough. The terms "myocardium" and "heart wall" are also used interchangeably. In addition, although the left ventricle is referred to throughout the description, it should be understood that the conduit described herein can be used to provide a passageway for the flow of blood from any heart chamber, not only the left ventricle.

The stent device is delivered either externally or internally through the coronary artery to a position distal to the blockage. At that position, the coronary artery, the myocardium and the wall of the left ventricle are pierced to provide a channel completely through from the coronary artery to the left ventricle of the heart. The stent is then positioned in the channel to provide a permanent passage for blood to flow between the left ventricle of the heart and the coronary artery, distal to the blockage. The stent is sized so that one open end is positioned within the coronary artery, while the other open end is positioned in the left ventricle. The hollow lumen of the stent provides a passage for the flow of blood.

The stent can be self-expandable or expanded by means of a balloon or similar device, and can be provided with various means to anchor it in position, such as expandable legs, hooks, barbs, flanges, collars, loops, wires, flares, suture holes and the like. The anchoring means can be adapted to anchor the conduit in the heart wall, or alternatively, in the coronary artery. The stent can be formed from a plurality of rings, which can be connected to provide stability. The stent can include a valve in its interior, and can also be used to deliver drugs or other pharmaceutical compounds directly into the myocardium and the coronary circulation.

Briefly stated, the methods and apparatus described and illustrated herein generally relate to direct coronary revascularization, wherein a conduit or opening is provided from the left ventricle to the coronary artery, oftentimes the left anterior descending (LAD), to provide blood flow directly therethrough. The conduit of the preferred embodiments has a distal top which is more preferably a ball top, wire top, flare top or flip-down top. These top configurations anchor the shunt at one end in the coronary artery.

BRIEF DESCRIPTION OF THE DRAWINGS

FIG. 22 is a perspective view of a ring of a bulkhead stent in a loaded configuration FIG. 23 is a perspective view of a ring of a bulkhead stent in an inserted configuration.

FIG. 24 is a perspective view of a bulkhead stent within a delivery catheter, showing the rings of the bulkhead stent being inserted.

FIG. 34F is a side view of a ball top shunt according to another embodiment of the present invention, the shunt being shown laid out flat.

FIG. 34G is a side view of the ball top shunt of FIG. 34F, shown implanted in a patient.

FIG. 40B is a side view of a flip-down shunt according to one embodiment of the present invention, the shunt being shown laid out flat.

FIG. 40C is a side view of the flip-down shunt of FIG. 40B, shown implanted in a patient.

FIG. 44B is a schematic side view of the distal end of the stent of FIG. 44A showing more particularly the web flange in the coronary artery.

FIG. 44C is a schematic side view of the stent and web flange of FIG. 44A showing a stylet holding the web flange closed.

DETAILED DESCRIPTION OF THE PREFERRED EMBODIMENT

Figure 1A:
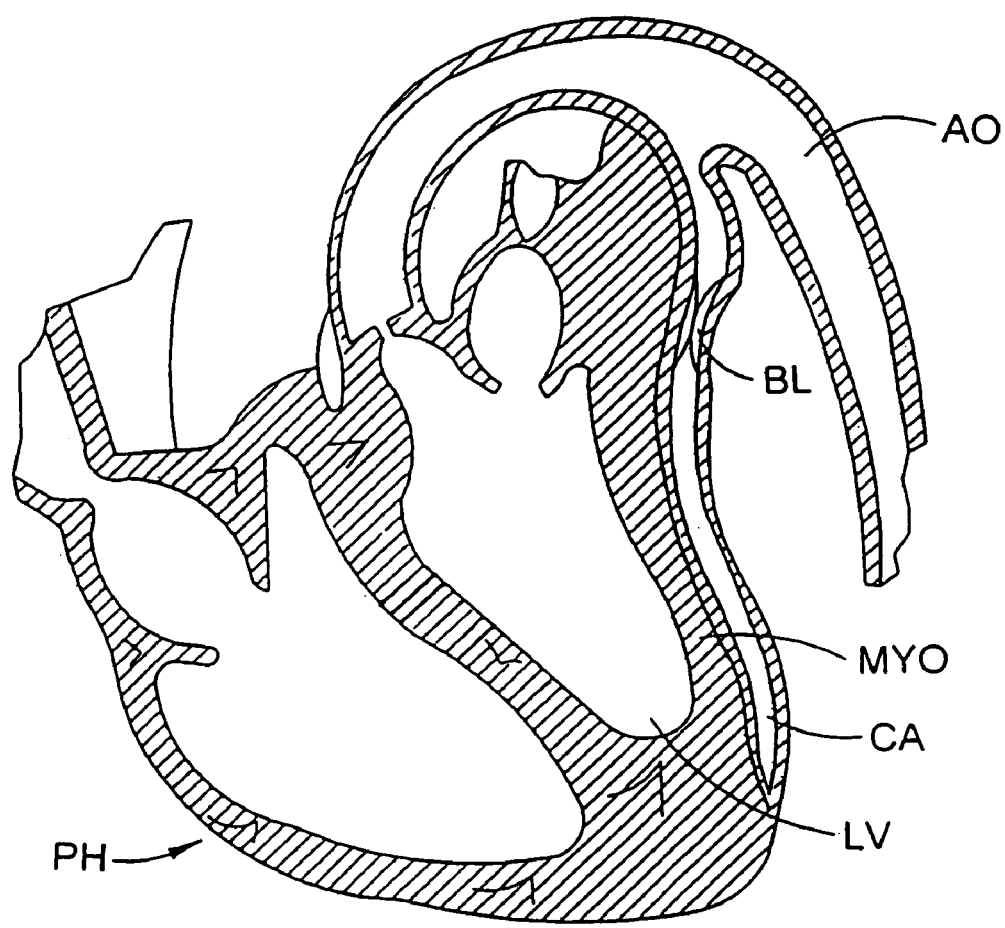
FIG. 1A is a cross-sectional view of a human heart, aorta and coronary artery.

As is well known, the coronary artery branches off the aorta and is positioned along the external surface of the heart wall. The anatomy of the human heart is illustrated in FIG. 1A. Oxygenated blood flows from the heart PH to the aorta AO, on to the rest of the body, some of the blood flowing into the coronary artery CA. In some individuals, plaque builds up within the coronary artery CA, blocking the free flow of blood and causing complications ranging from mild angina to heart attack and death.

In order to restore the flow of oxygenated blood through the coronary artery, one embodiment of the present invention provides for the shunting of blood directly from the heart to a site in the coronary artery that is distal to the blockage. A channel is formed through the wall of the coronary artery and the myocardium and into the left ventricle of the heart that lies beneath the coronary artery. A stent or conduit is positioned in the passage to keep it open, and allow for the flow of oxygenated blood directly from the heart into the coronary artery. Again, it should be understood that while the insertion of the conduit in the myocardium between the left ventricle and the coronary artery is described in detail below, this is merely exemplary and use of the conduit between other chambers of the heart and the coronary artery, and between blood vessels is also contemplated.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In some individuals, aortic insufficiency or peripheral venous insufficiency occurs. Aortic insufficiency is the leakage of blood through the aortic valve, resulting in a backflow of blood into the left ventricle. The heart compensates for the backflow of blood by pumping harder, resulting in hypertrophy (thickening of the heart muscle) and dilation of the left ventricle wall. Left untreated, heart failure can result. In venous insufficiency, the heart valves are unable to prevent the backflow of blood. This too can result in heart failure. Accordingly, one embodiment of the invention provides for the use of a conduit placed within the heart wall to improve the flow of oxygenated blood through the body.

Balloon Expanded Stent

Figure 1B:
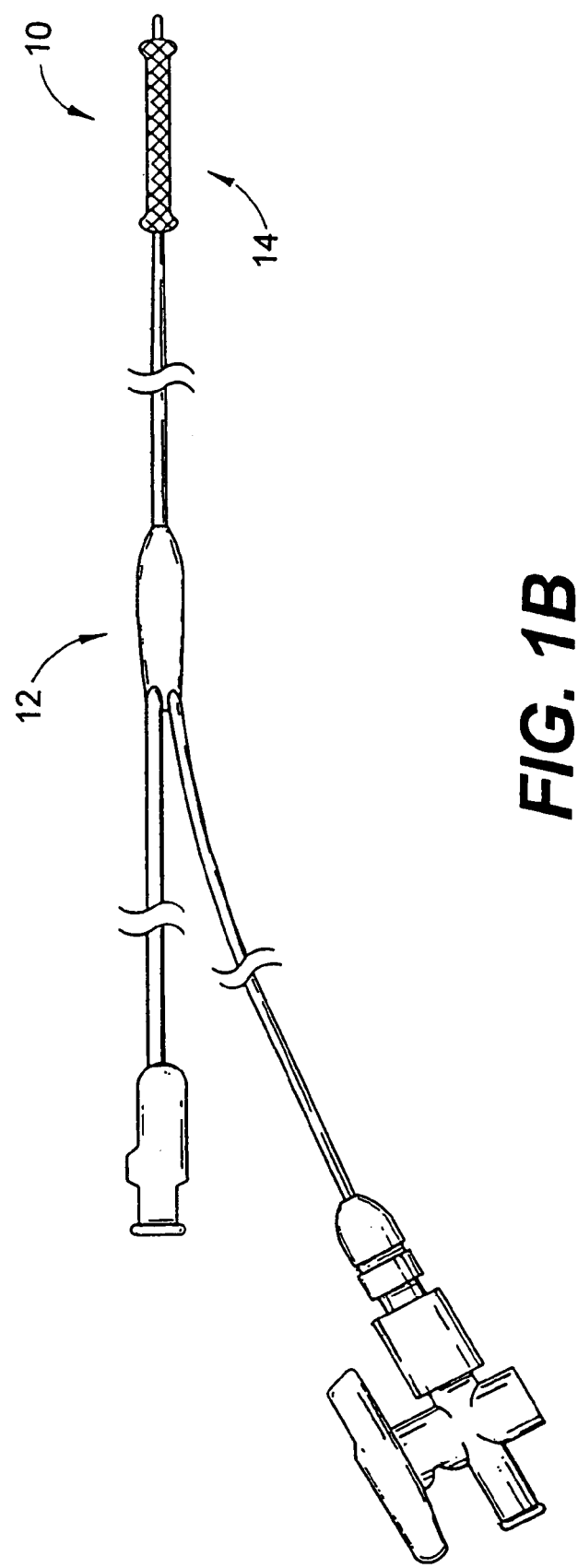
FIG. 1B is a side view of one embodiment of an expandable stent and the balloon catheter used for stent delivery.
Figure 2:
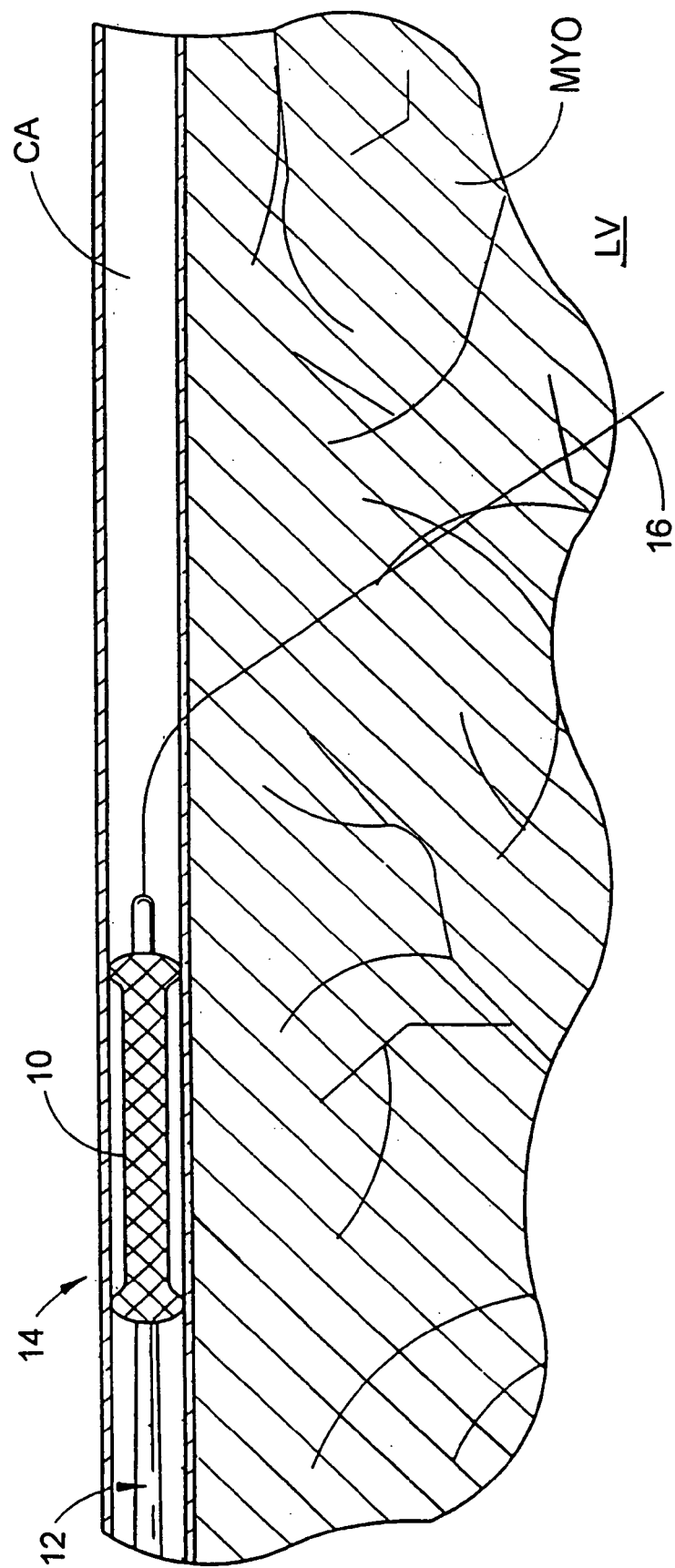
FIG. 2 is a side view of the stent of FIG. 1B mounted on the distal end of the catheter for delivery into the myocardium, with the coronary artery and myocardium shown cut-away.

A first embodiment of the present invention is illustrated in FIG. 1B. This embodiment is a balloon-expanded stent 10. The stent 10 is introduced as described below, using a high-pressure balloon catheter 12 to deploy the stent 10 once it is properly positioned in the myocardium MYO (FIG. 2). When the stent 10 is positioned inside the myocardial wall MYO, the balloon 14 is inflated to expand the stent 10 and open the conduit from the left ventricle LV into the coronary artery CA. The stent 10 can include attachment mechanisms not limited to hooks, barbs, flanges, large collars, suture holes and/or other means to ensure a seal is created between the coronary artery CA and the wall of the myocardium MYO and to prevent the threat of stent 10 migration. When the attachment of the stent 10 is completed, the remaining catheter assembly 12 is removed, leaving the stent 10 in place. Upon deflating the balloon 14, the stent 10 will remain open. Because of the shape of this stent 10, a dumbbell shaped balloon 14 is preferably used to ensure proper expansion, as described below.

FIGS. 1B through 4 illustrate the introduction of the balloon-expanded stent 10 into the myocardial wall MYO. FIG. 1B illustrates the stent 10 mounted over the balloon 14 on the distal end of the stent introducer catheter 12. FIG. 2 illustrates the stent introducer catheter 12 following the path created by a puncture wire 16 extending past the distal end of the introducer catheter 12, and used to access the left ventricle LV through the coronary artery CA and myocardium MYO.

Figure 3:
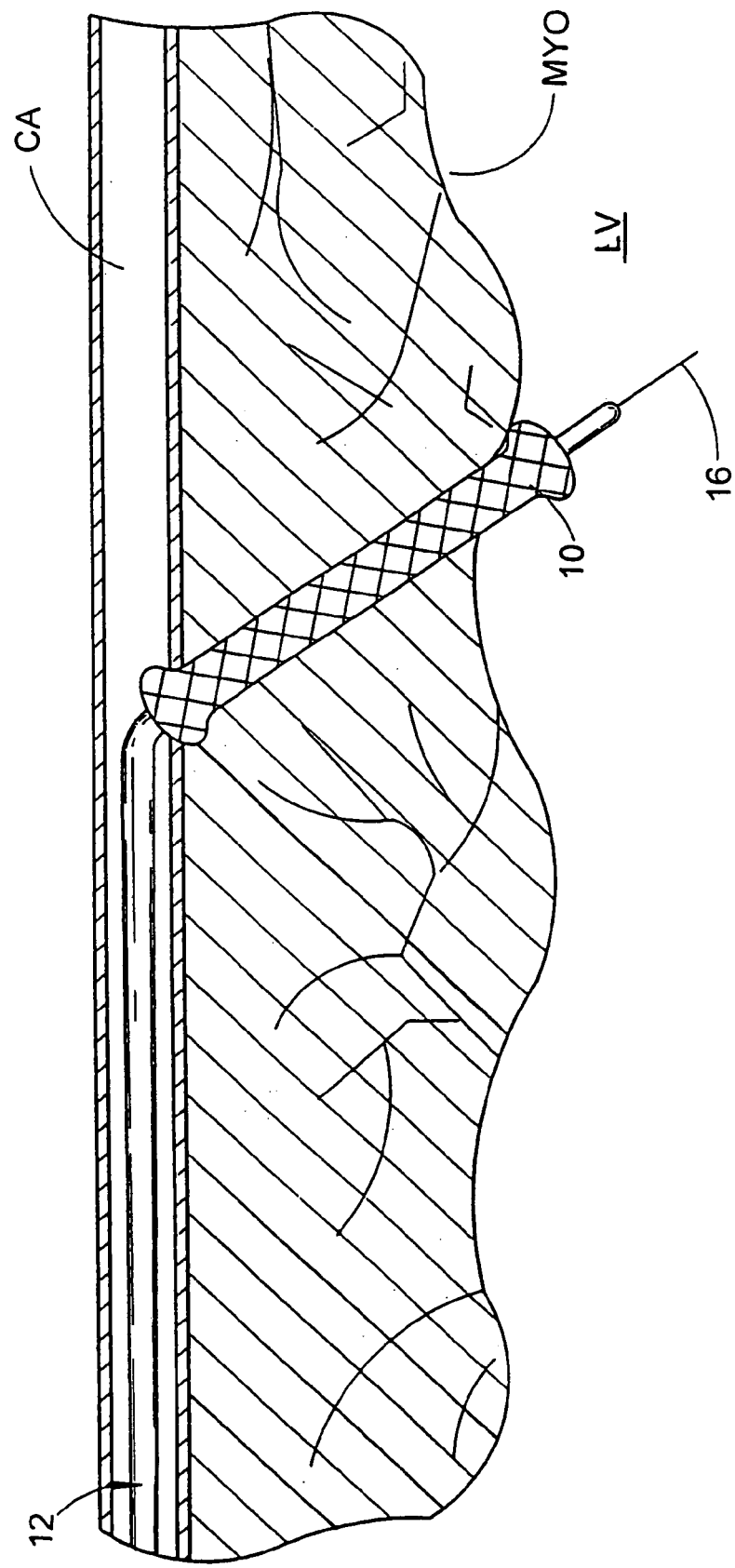
FIG. 3 is a side view of the distal end of the stent/catheter assembly of FIG. 1B positioned in the myocardium, with the coronary artery and myocardium shown cut-away.
Figure 4:
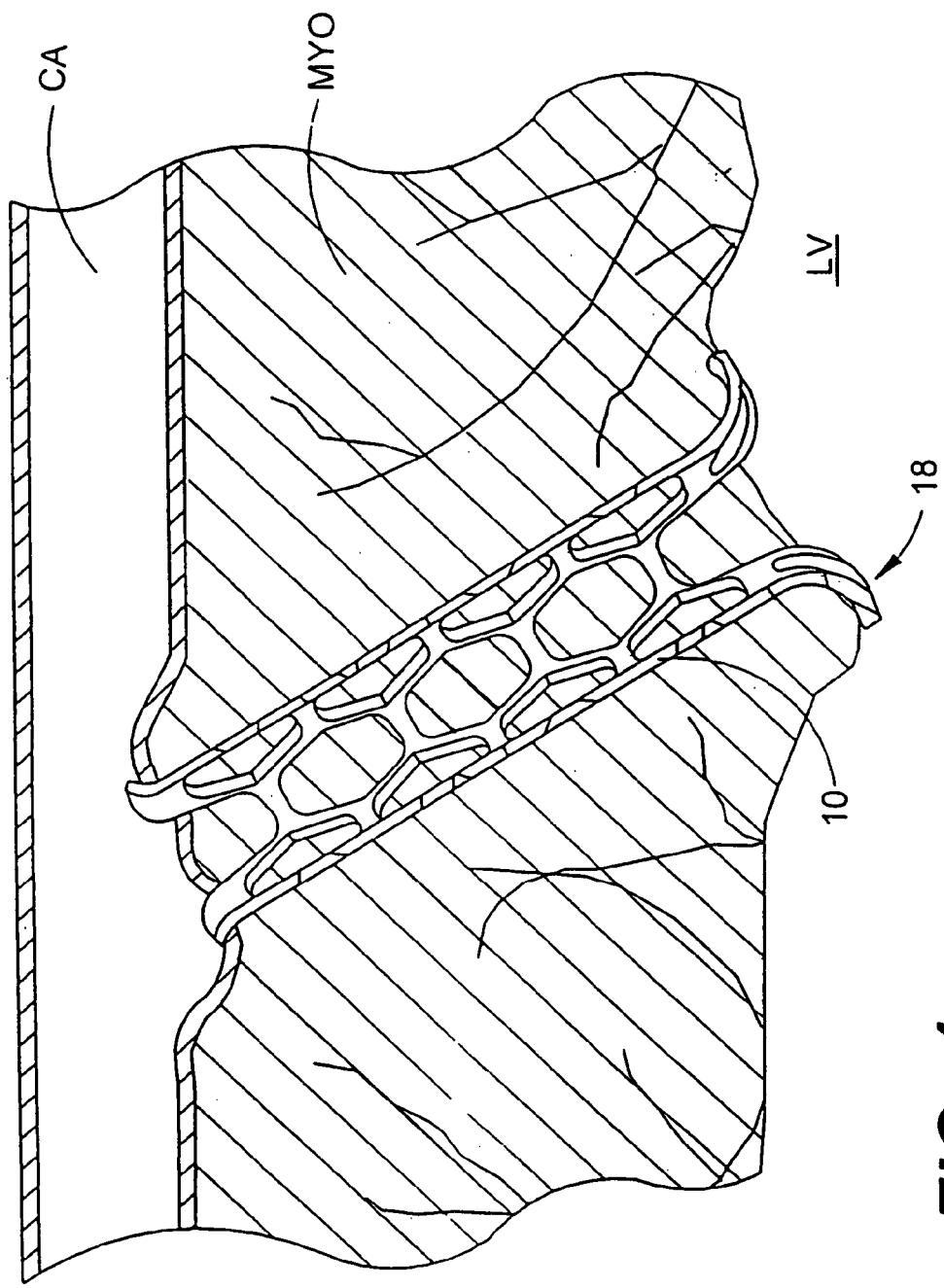
FIG. 4 is a cross-sectional side view of the stent of FIG. 1B positioned within the myocardium after removal of the catheter used for delivery.

FIG. 3 illustrates the non-expanded stent 10 positioned inside the myocardial wall MYO prior to inflation of the balloon 14. FIG. 4 illustrates an expanded stent 10 in position, with the introducer catheter 12 removed. Because of the way the attachment mechanisms 18 expand on this stent 10, a dumbbell shaped balloon 14 is preferably used to flare out the ends of the stent 10. These flared edges 18 maintain the stent 10 in its proper position in the heart wall MYO and provide a seal between the coronary artery CA and the outer heart wall MYO.

Self Expanding Stent

The second embodiment of the stent or conduit incorporates a self-expanding stent 20, illustrated in FIGS. 5-8. The stent 20, having a retaining sheath 26 to hold it in a non-expanded configuration, is introduced into the wall of the myocardium MYO as follows. The stent delivery catheter 22 is advanced over a puncture mechanism 24 and into the wall of the myocardium MYO as described above. When the stent 20 is properly seated in the myocardial wall MYO, its retaining sheath 26 is withdrawn, allowing the stent 20 to expand and open a conduit from the ventricle LV to the coronary artery CA. This stent 20 also includes attachment mechanisms not limited to hooks, barbs, flanges, large collars, suture holes and/or other means to ensure a seal is created between the artery CA and the wall of the myocardium MYO, and to prevent the threat of stent 20 migration. When the positioning is completed, the remaining catheter assembly 22 is removed, leaving the stent 20 in place.

Figure 5:
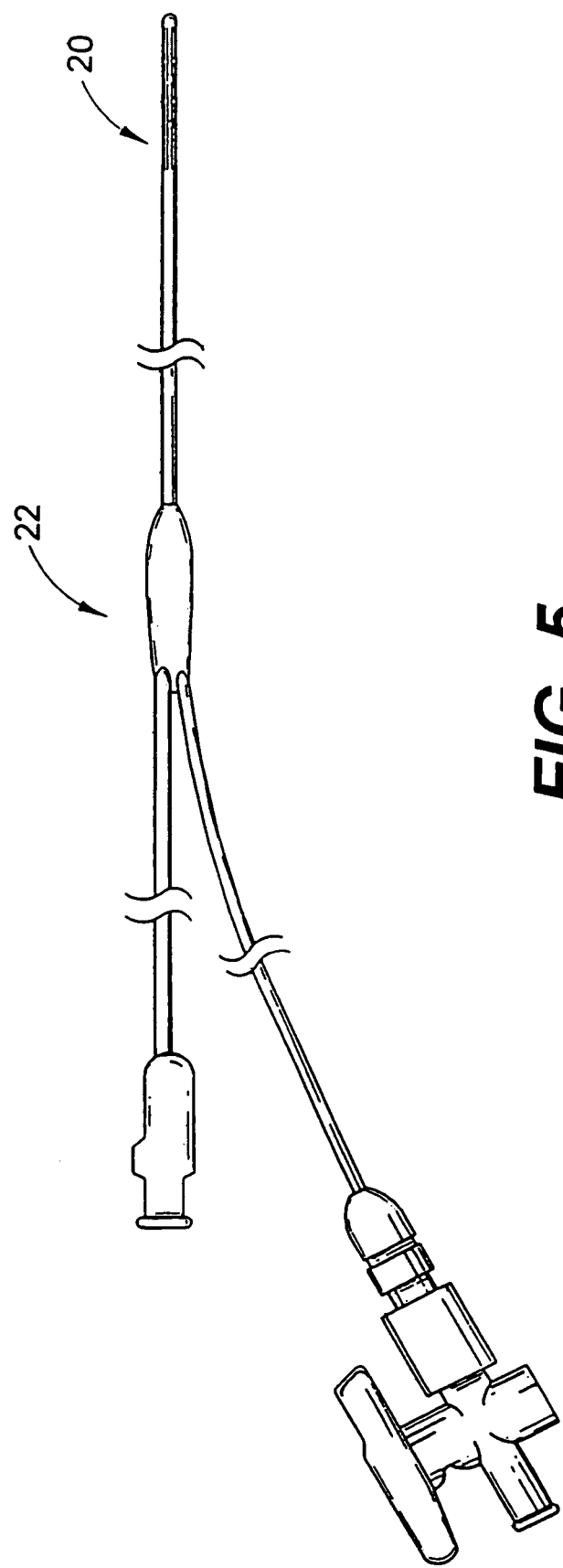
FIG. 5 is a side view of another embodiment of the stent and the catheter used for stent delivery.
Figure 6:
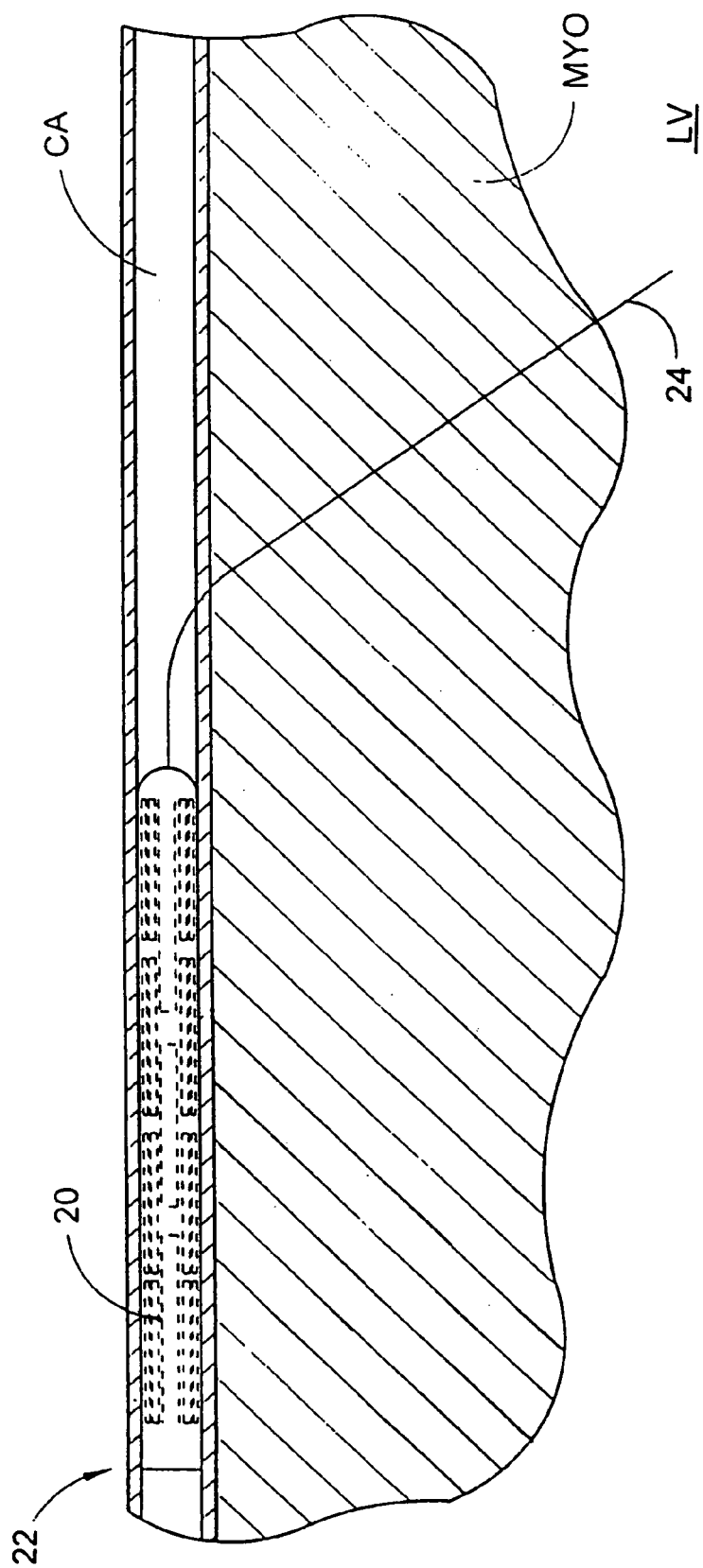
FIG. 6 is a cross-sectional side view of the catheter and puncture device used to introduce the self-expanding stent of FIG. 5 into the myocardium.
Figure 7:
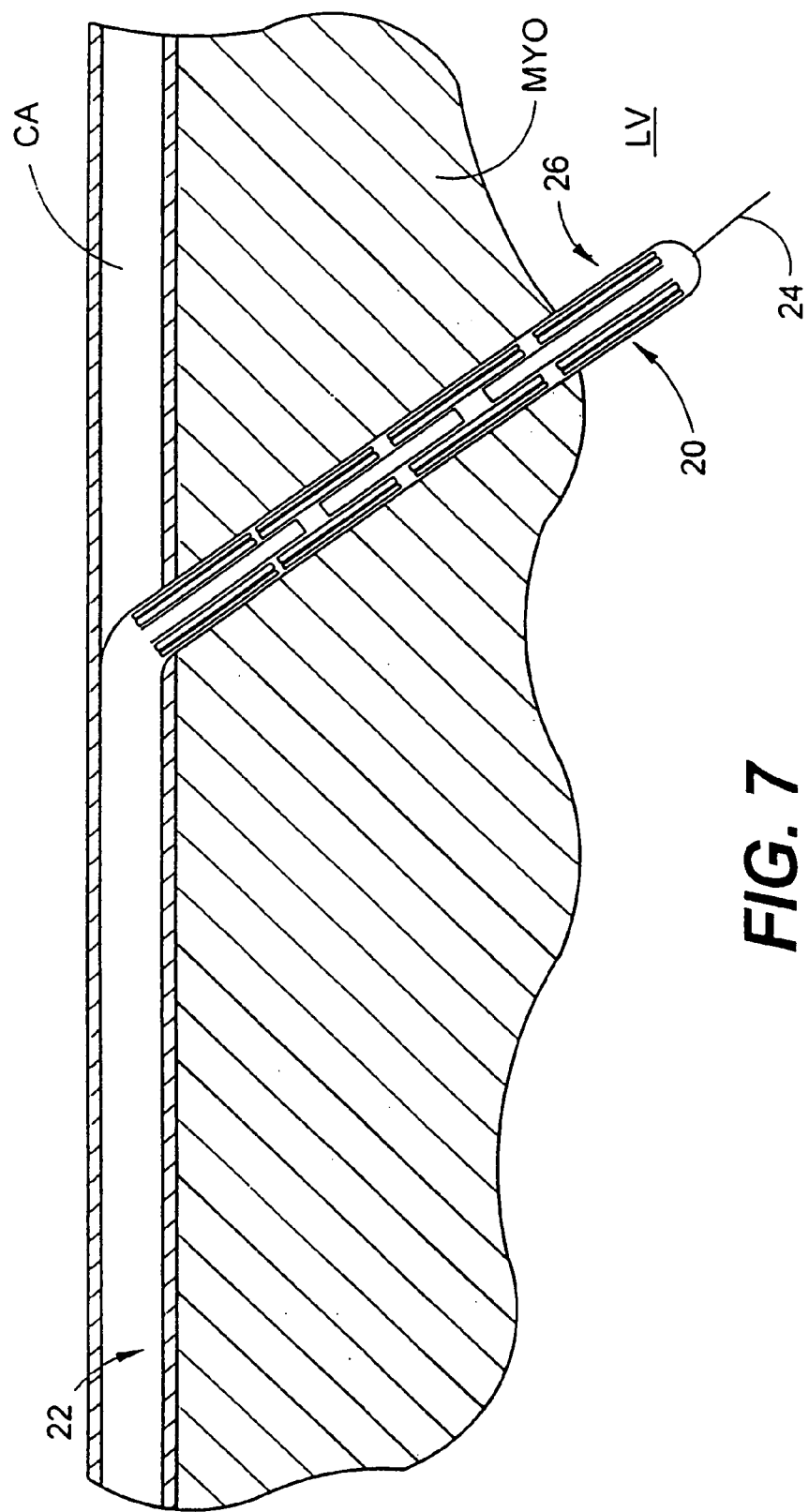
FIG. 7 is a cross-sectional side view of the stent/catheter assembly of FIG. 5 positioned in the myocardium.
Figure 8:
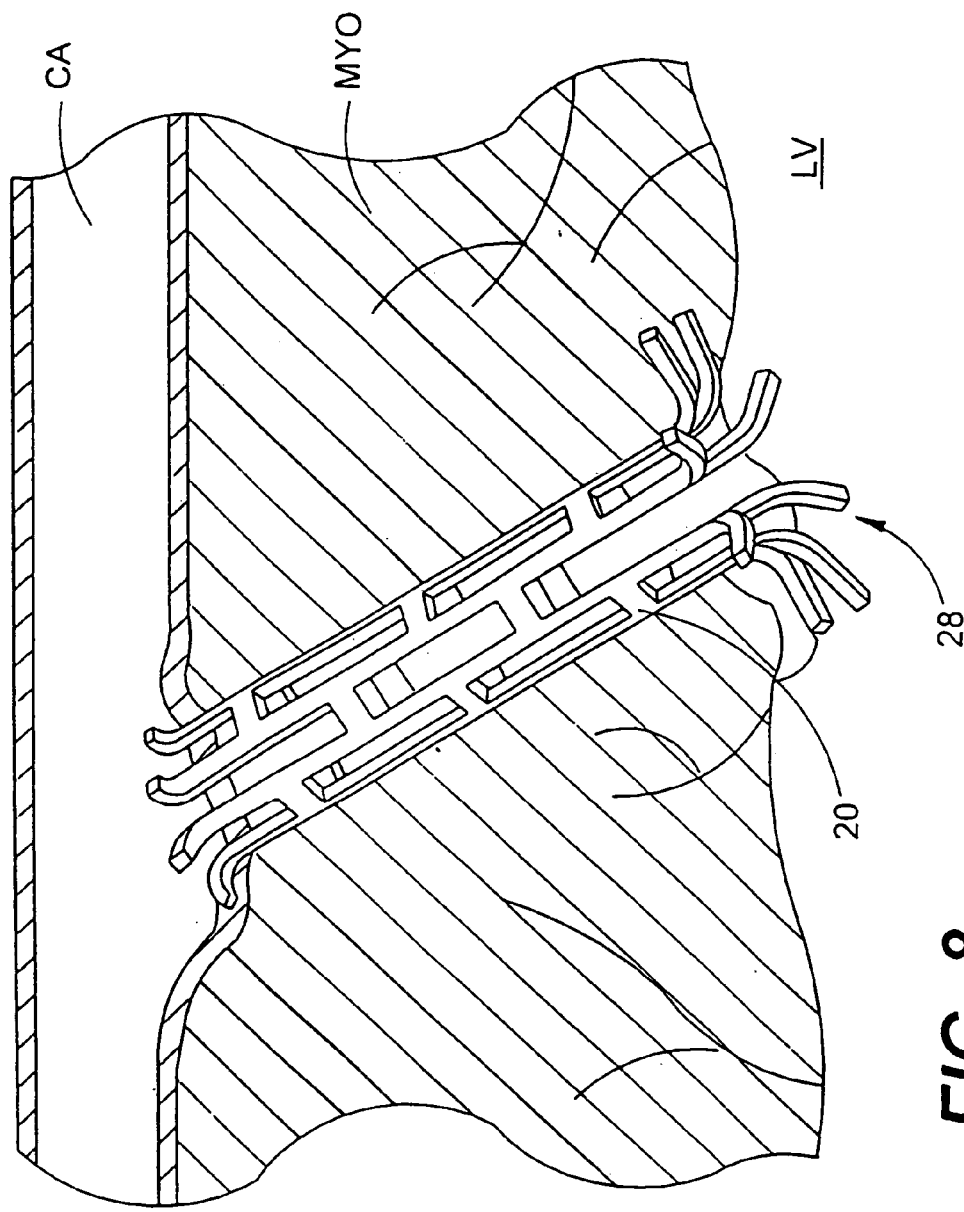
FIG. 8 is a side view of the self-expanding stent of FIG. 5 positioned within the myocardium after removal of the catheter and puncture device, with the coronary artery and myocardium shown cut-away.

The self-expanding stent 20 mounted on the distal end of the stent introducer catheter 22 is illustrated in FIG. 5. FIG. 6 illustrates the stent introducer 22 following the path created by a puncture wire 24 used to form the passage between the coronary artery CA and the left ventricle LV. FIG. 7 illustrates a non-expanded stent 20 located in position on the stent introducer catheter 22 with the introducer catheter 22 in position in the heart wall MYO. FIG. 8 illustrates the self-expanding stent 20 in position, with the introducing catheter 22 removed. Flared edges 28 on the stent 20 maintain its proper position in the heart wall MYO and provide a seal between the coronary vessel CA and outer surface of the heart MYO.

For the stent designs described above, additional anchoring methods may be desired to maintain the stent's proper position and/or create a leak-free seal in the coronary artery. Suitable attachment mechanisms include a set of barbs located on the stent body or flares and a collar on the coronary side to help seal and prevent blood from exiting the gap between the vessel and outer heart wall. The stent can also be anchored in place by applying sutures. The stent can include holes at either end to facilitate the placement of these anchoring sutures. A suture gun can be used to apply multiple sutures at the same time. In addition, the stents can be lined, if desired, with materials such as polymers, for example polytetrafluoroethylene (PTFE), silicone or GORTEX, to provide for the ease of blood flow therethrough.

Stent with Attachment Flanges

Figure 9:
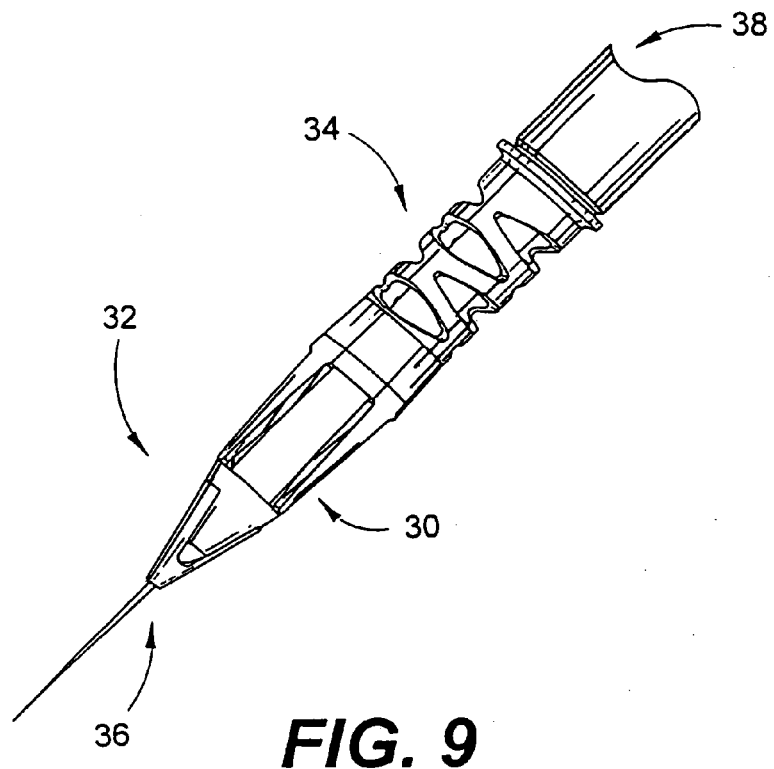
FIG. 9 is a perspective view of another embodiment of the stent having expandable legs, showing the stent mounted on the distal end of the introducer catheter.
Figure 10:
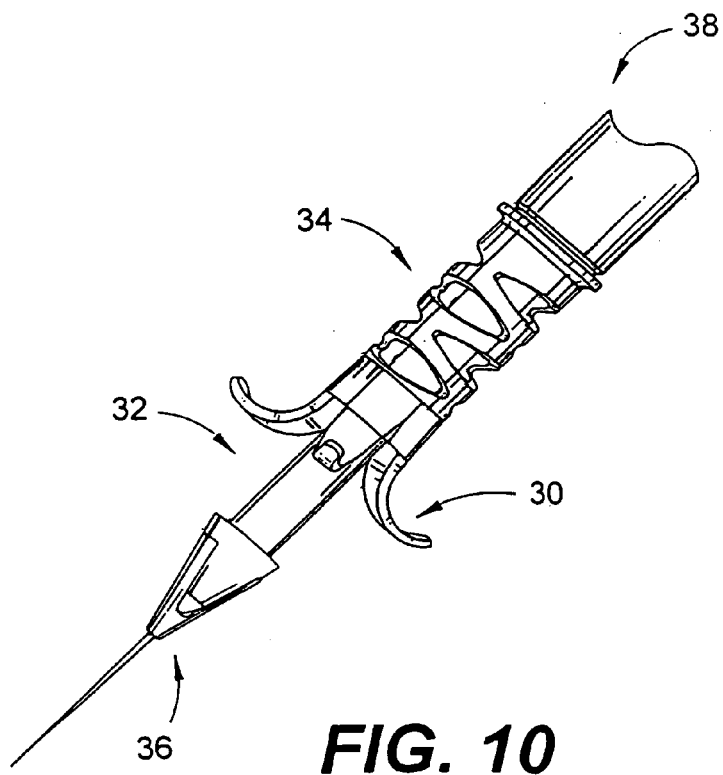
FIG. 10 is a perspective view of the stent of FIG. 9, showing the distal end of the introducer catheter pushed forward to allow the legs of the stent to expand.
Figure 11:
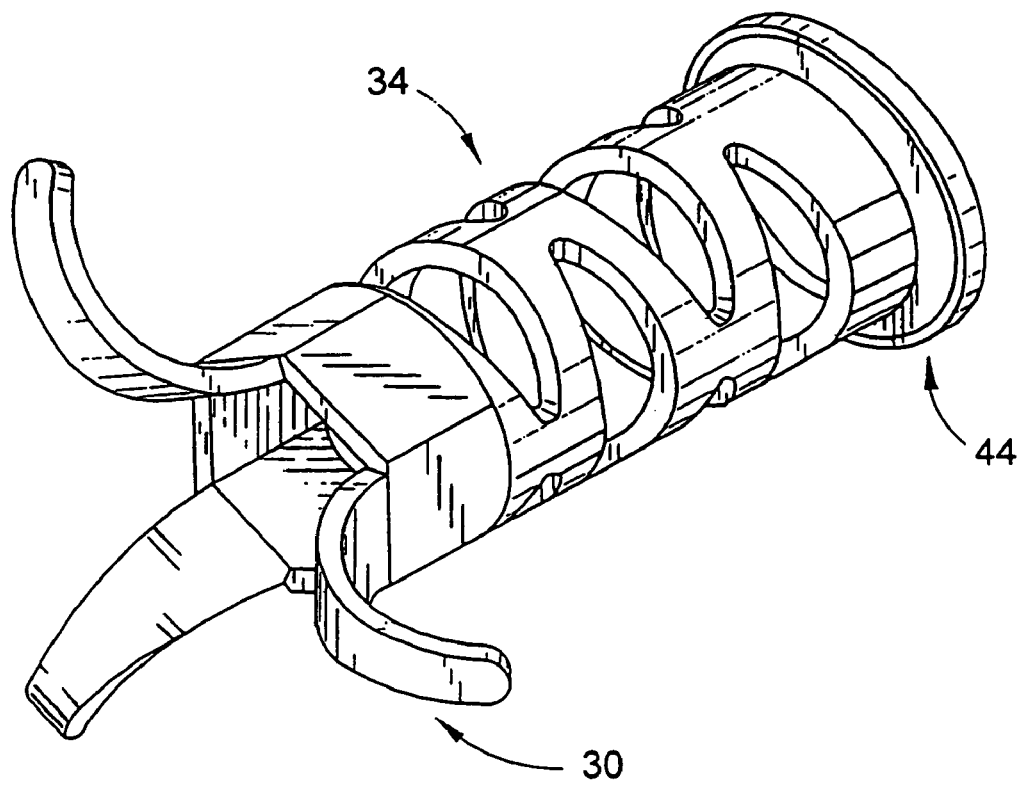
FIG. 11 is a perspective view of the stent of FIG. 9, showing the legs of the stent in an expanded position.

A third embodiment of the stent design, illustrated in FIGS. 9-11, incorporates attachment flanges or "legs" 30 that expand after introduction into the myocardium to hold the stent 34 in place. The puncture instrument 32 and stent 34 are mated together and are advanced into the myocardial wall as a single unit. The puncture instrument's distal end 36 is shaped in a "nose-cone" configuration, which is responsible for containing the legs 30 of the stent 34 while it is being introduced into the wall of the myocardium. When the stent 34 is in the proper position in the myocardial wall, the nose cone 36 is pushed forward, releasing the attachment legs 30 of the stent 34. The internal diameter (ID) of the stent 34 is large enough to allow the nose cone 36 to pass back through. The stent 34 is then released from the catheter 38 and the catheter 38 is removed.

FIG. 9 illustrates the stent 34 mounted on the introducer catheter 38. The expanding legs 30 of the stent 34 are held in place by the nose cone 36 on the distal end of the catheter 38 that acts as a dilator. The catheter assembly 38 is advanced over a puncture wire if desired, into proper position in the myocardium, and the nose cone 36 is pushed forward allowing the legs 30 to expand as shown in FIG. 10. The nose-cone/puncture assembly 32, 36 is then withdrawn through the lumen of the stent 34. When the nose-cone/puncture assembly 32, 36 is removed, the stent 34 can be pushed off the introducer catheter 38 and remains in the myocardium in the position shown in FIG. 11. FIG. 11 also illustrates a sealing collar 44 that may be used in the interface between the coronary artery and the outer wall of the heart to prevent hemorrhaging around the stent 34 and to hold the stent 34 in place. Sutures can be used to ensure that the stent is maintained in its proper position and prevent migration.

Biodegradable Stent

Figure 13:
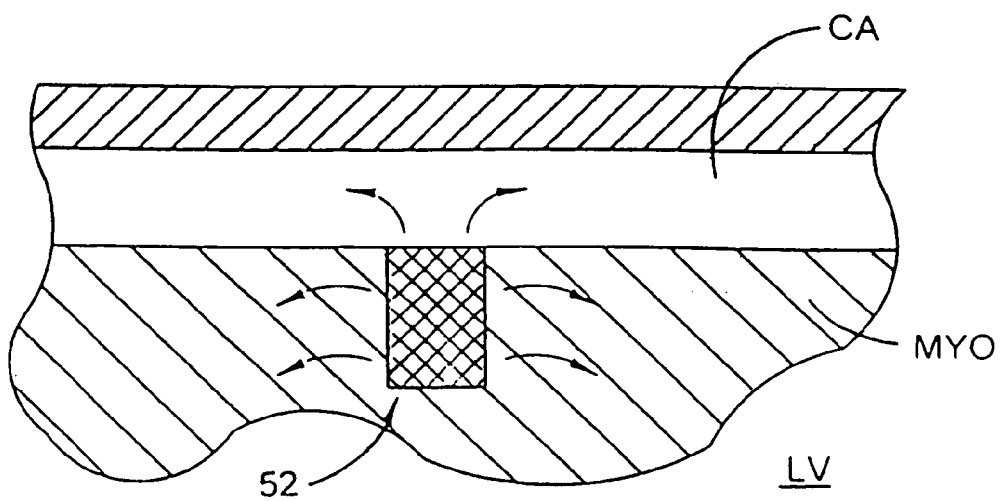
FIG. 13 is a side view of a biodegradable stent positioned within the myocardium, with the coronary artery and myocardium shown cut-away.

If desired, the stent or conduit of the present invention can be formed of biodegradable or bioabsorbable materials and/or used to deliver drugs directly into the myocardium and the coronary circulation. Such a stent 52 is illustrated in FIG. 13. The biodegradable stent 52 can extend only partially through the myocardium MYO as illustrated in FIG. 13, but can also extend entirely through from the left ventricle LV to the coronary artery CA. Once positioned in the myocardium MYO, the stent 52 degrades, dissolves or is absorbed over time to release drugs, genes, angiogenesis or growth factors, or other pharmaceutical compounds directly into the heart muscle MYO and the coronary artery CA, as shown by the arrows in FIG. 13. Bioabsorbable materials include, but are not limited to, polymers of the linear aliphatic polyester and glycolide families, such as polylactide and polyglycolide.

Bulkhead Stent

Figure 12:
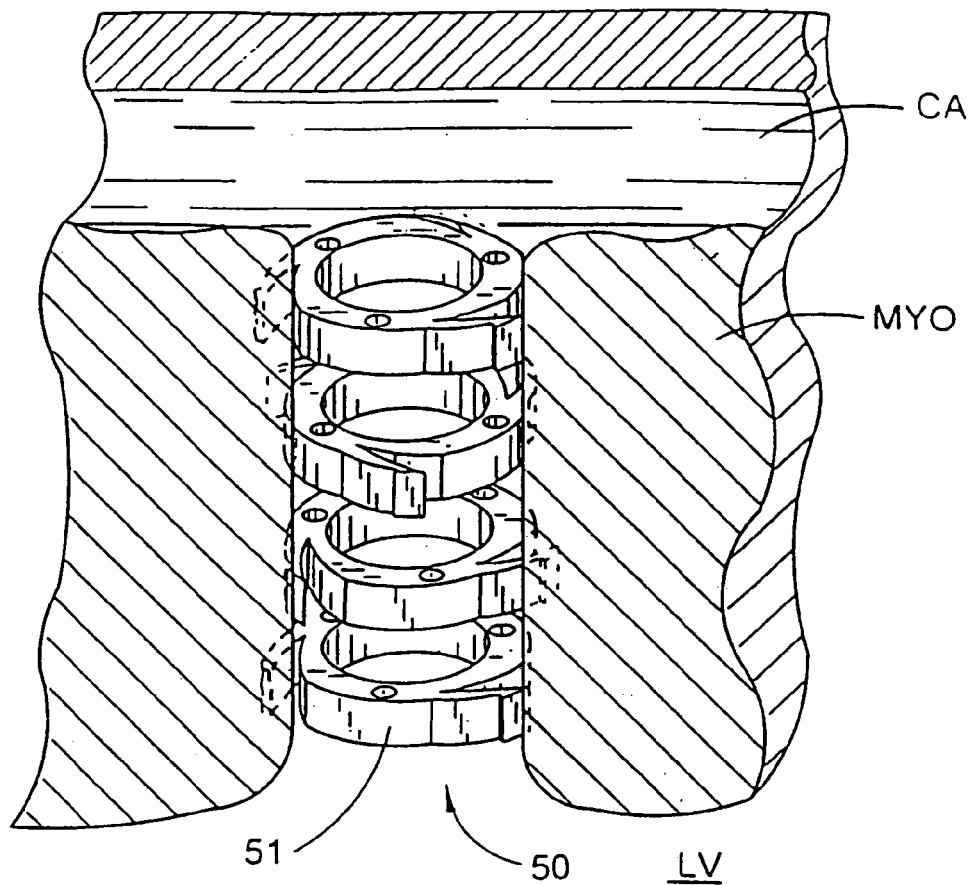
FIG. 12 is a side view of another embodiment of the stent positioned within the myocardium, with the coronary artery and myocardium shown cut-away.

FIG. 12 illustrates a further embodiment of the present invention, a "bulkhead" stent 50. This stent 50 consists of a plurality of rings, which are placed in the myocardium MYO. The rings 50 form a passage through which blood flows from a chamber in the heart, such as the left ventricle LV, directly into the coronary artery CA. The stent 50 is preferably formed of biocompatible material such as a metal or polymer. A gun or other suitable device can be used to implant the stent 50 in the myocardium MYO.

If desired, the separate units or rings of the stent 50 can be connected via a wire, suture thread, or similar means. The wire is threaded through the holes 51 located in each ring. Connecting the rings of the stent 50 in this manner serves to make the stent 50 more stable and to prevent the migration of the individual units. If desired, a valve (not shown) can be incorporated into the stent 50 to help prevent the backflow of blood into the left ventricle LV.

Figure 14:
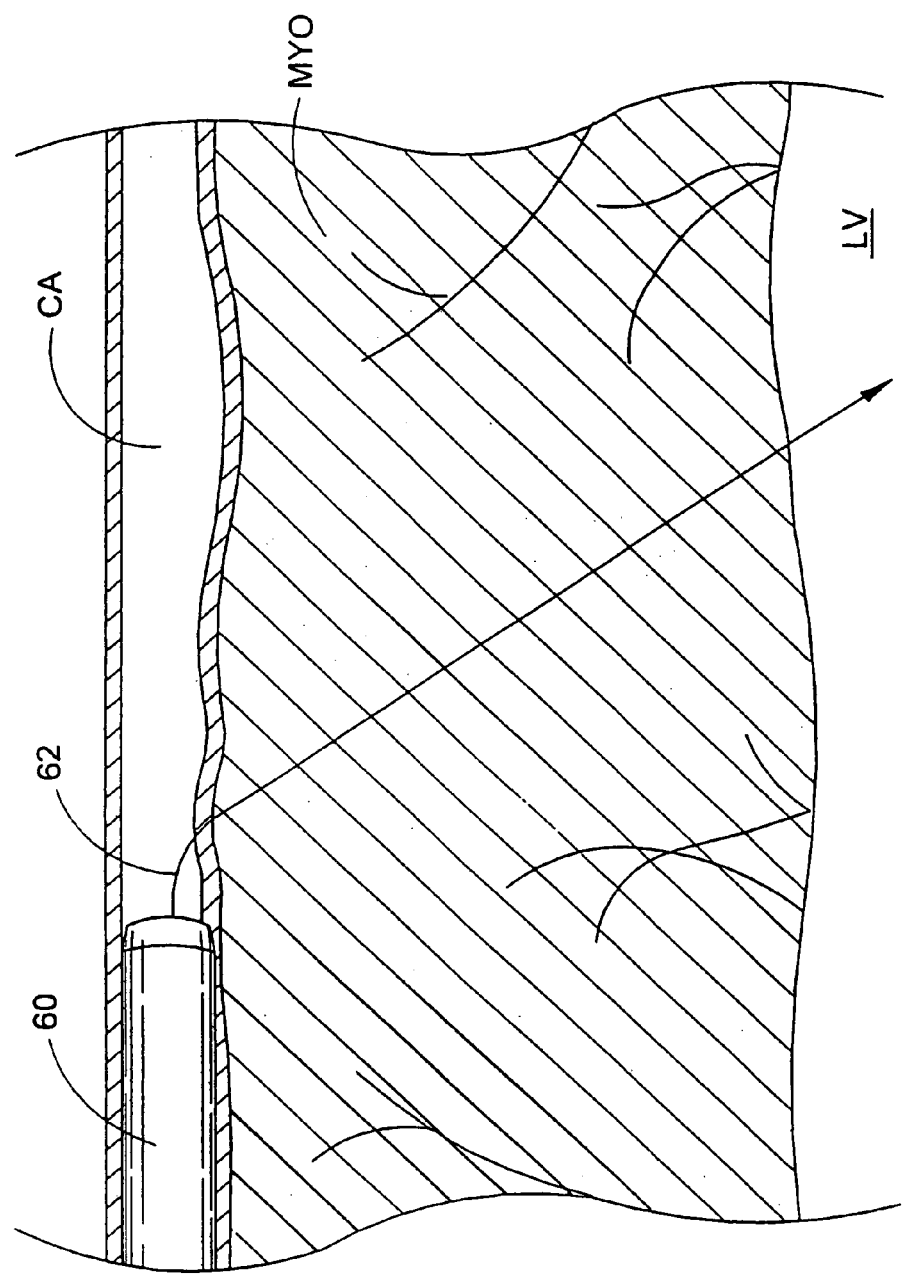
FIG. 14 is a side view of a catheter and puncture device used to introduce a bulkhead stent into the myocardium, with the coronary artery and myocardium shown cut-away.
Figure 15:
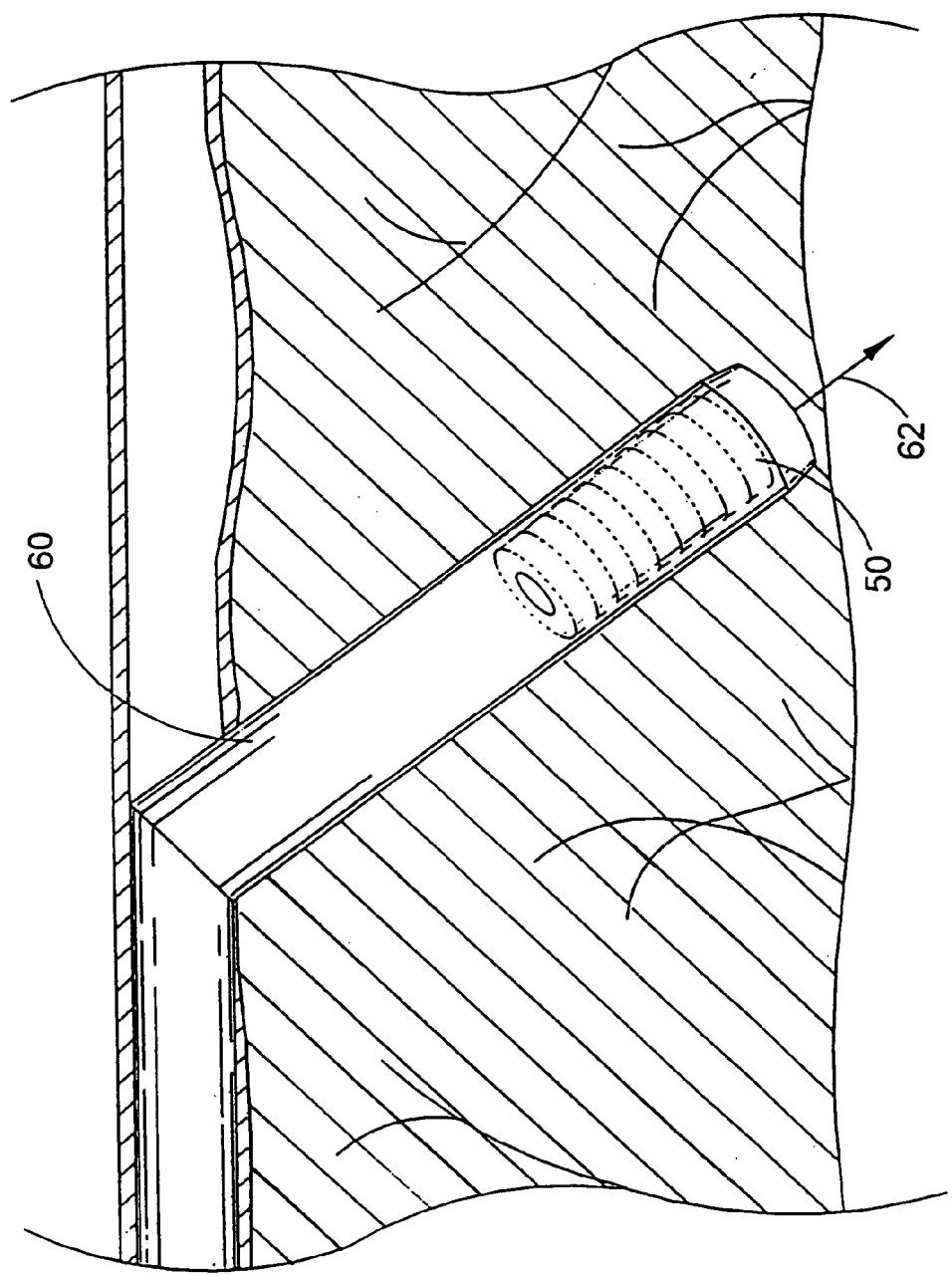
FIG. 15 is a side view of the stent/catheter assembly of FIG. 14 positioned in the myocardium, with the coronary artery and myocardium shown cut-away.
Figure 16:
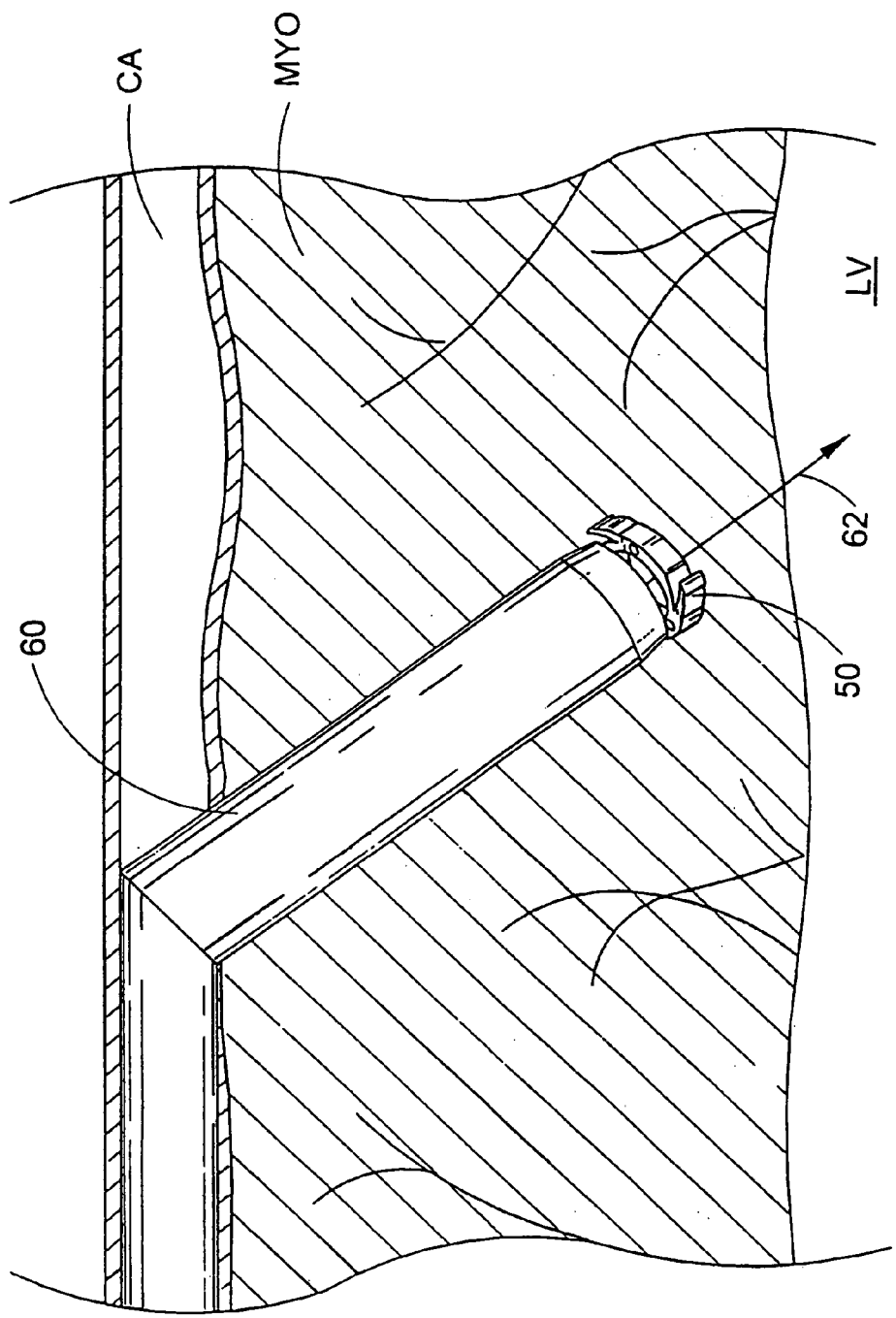
FIGS. 16-19 are progressive side views of the stent/catheter assembly of FIG. 14, showing the bulkhead stent being deployed into the myocardium.
Figure 17:
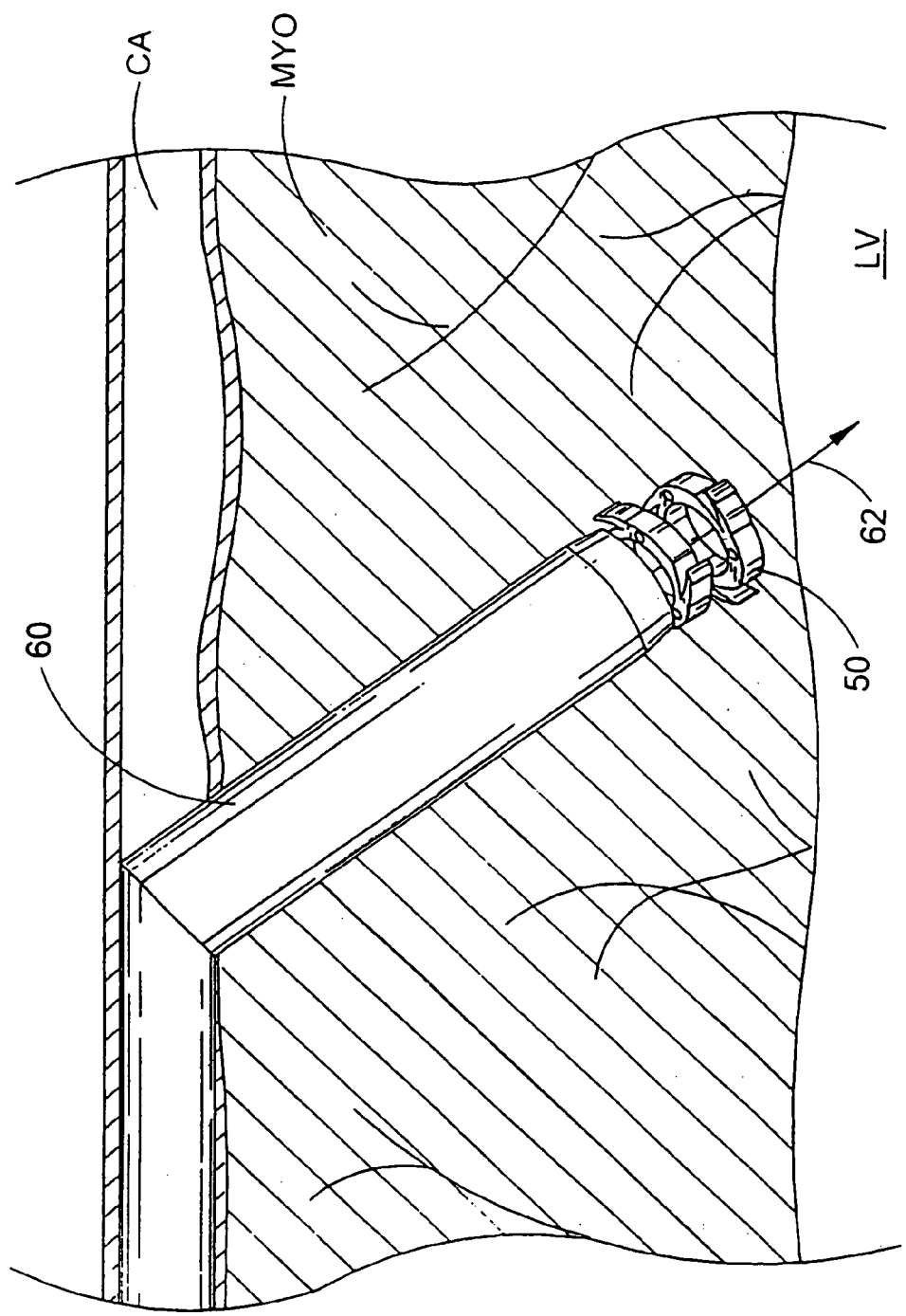

Turning now to FIGS. 14-26, there is illustrated in greater detail one preferred method and apparatus for providing a bulkhead stent 50, as shown in FIG. 12, into the myocardium MYO. As shown in FIG. 14, a stent delivery catheter 60 is advanced over a puncture wire 62 and into the wall of the myocardium MYO as described above. The stent delivery catheter 60 follows the path created by the puncture wire 62 used to form the passage between the coronary artery CA and the left ventricle LV. FIG. 15 illustrates a bulkhead stent 50 still located in position inside the stent delivery catheter 60 with the catheter 60 in position in the heart wall MYO.

Figure 18:
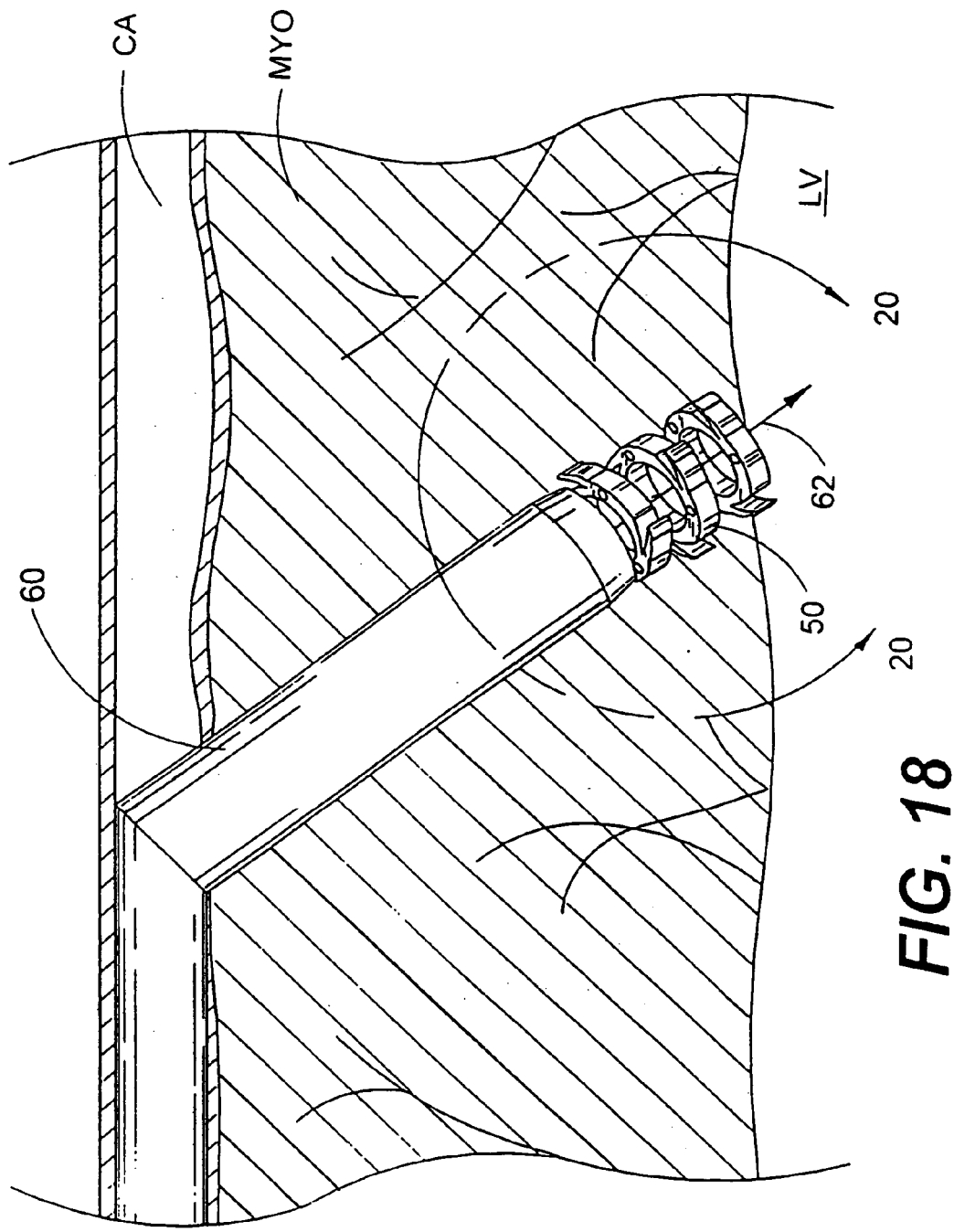
Figure 19:
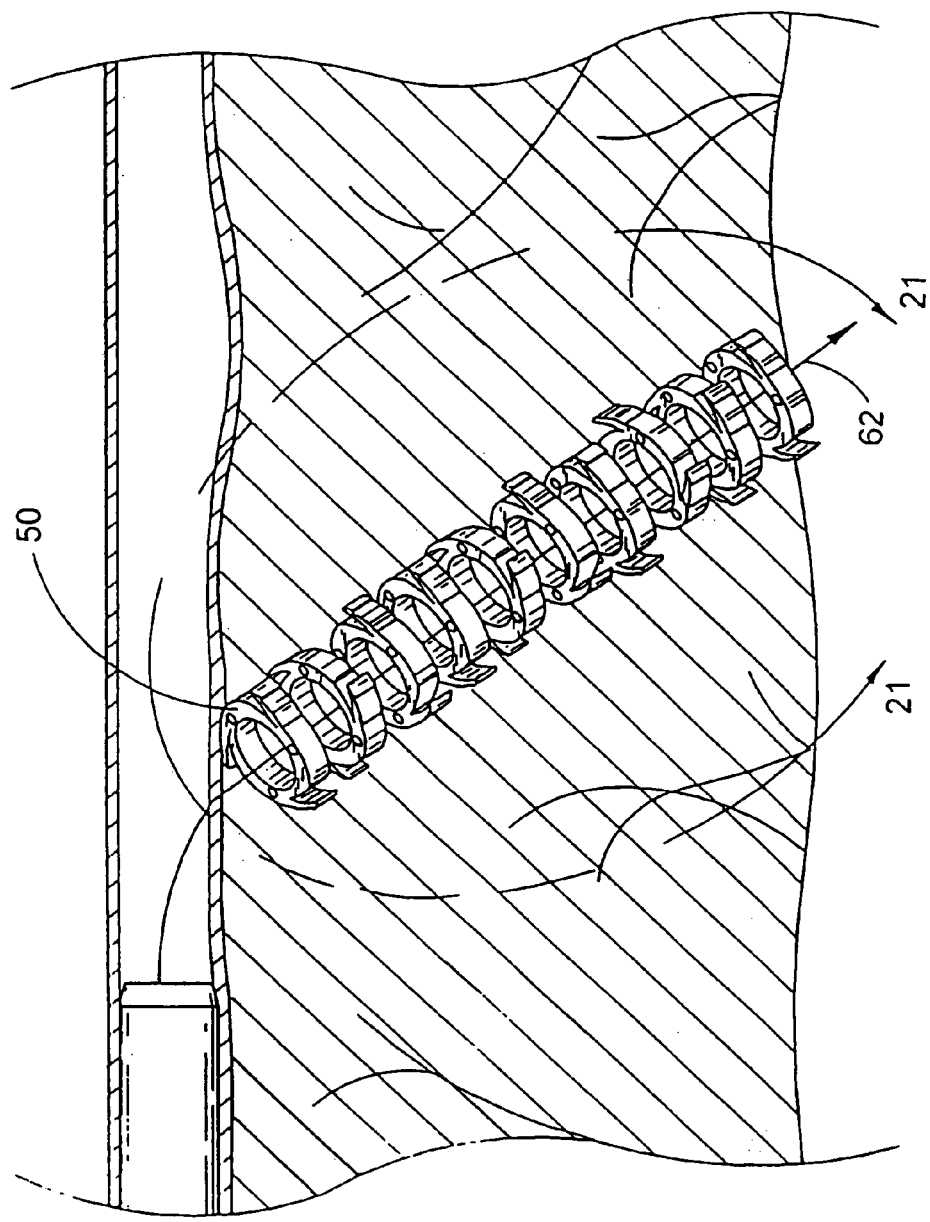
Figure 20:
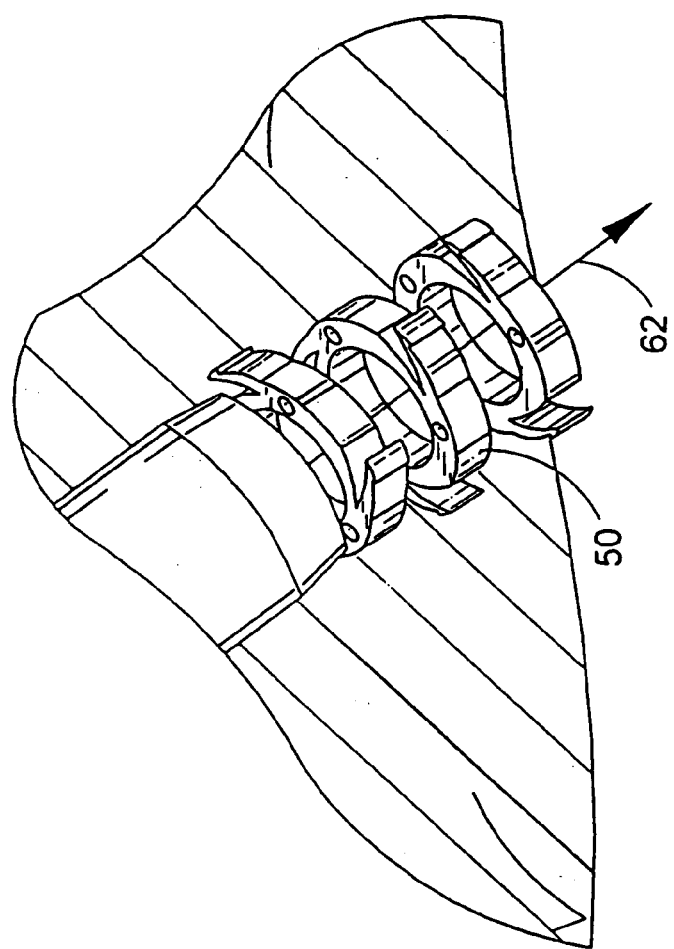
FIGS. 20 and 21 are enlarged views of FIGS. 18 and 19, respectively, showing the bulkhead stent being deployed into the myocardium.
Figure 21:
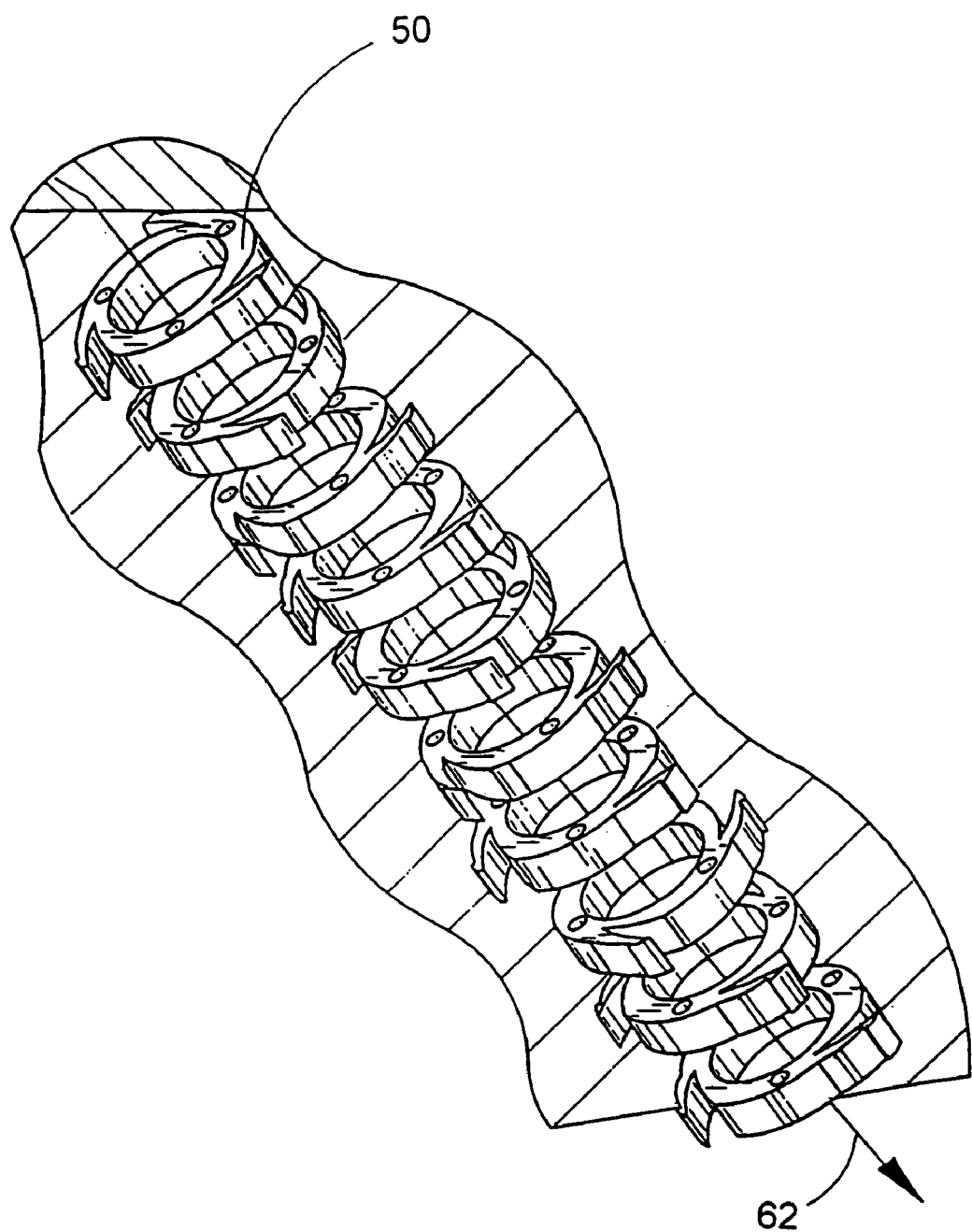
Figure 25:
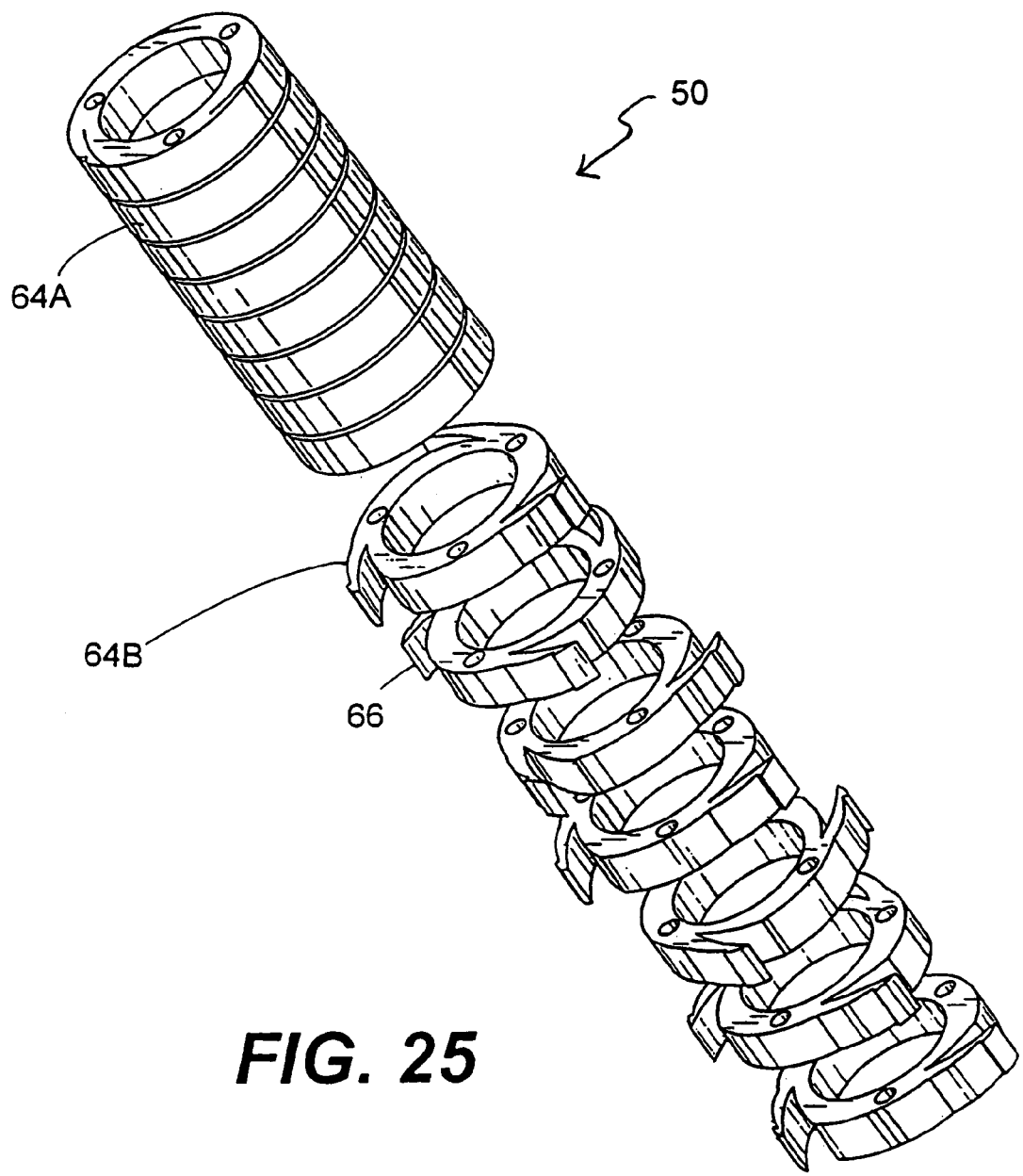
FIG. 25 is a perspective view of a bulkhead stent, with the rings of the stent in loaded and inserted configurations.

FIGS. 16-19 show one embodiment for deploying the bulkhead stent 50 into the myocardium MYO. As the delivery catheter 60 is retracted proximally from the myocardium MYO, the rings comprising the bulkhead stent 50 are deployed into the myocardium MYO. FIGS. 20 and 21 are enlarged views of FIGS. 18 and 19, showing the rings of the bulkhead stent 50 positioned within the myocardium MYO to form the passageway therethrough.

FIGS. 22-25 illustrate more particularly the structure and deployment of the rings comprising the bulkhead stent 50. As shown in FIG. 24, the bulkhead stent comprises a plurality of rings 64 that are initially loaded into the delivery catheter 60. While inside the lumen of the catheter 60, each ring 64 has a loaded configuration 64A, shown in FIGS. 22 and 25. After ejectment from the catheter 60, the ring 64 assumes an inserted configuration 64B, shown in FIGS. 23 and 25. Preferably, the inserted configuration of ring 64B includes a plurality of flanges 66 around the circumference of each ring 64, thereby providing a securement mechanism to anchor each ring 64 to the myocardium MYO. Each ring 64 transforms from its loaded configuration 64A to its inserted configuration 64B by virtue of being released from the catheter 60. Specifically, the catheter 60 acts as a restraint on each ring 64 to keep it in its loaded configuration 64A. Then, once the ring 64 is released from the catheter 60, the flanges 66 provided along the circumference of each ring 64 are allowed to extend outward to provide the securement mechanism.

Figure 26:
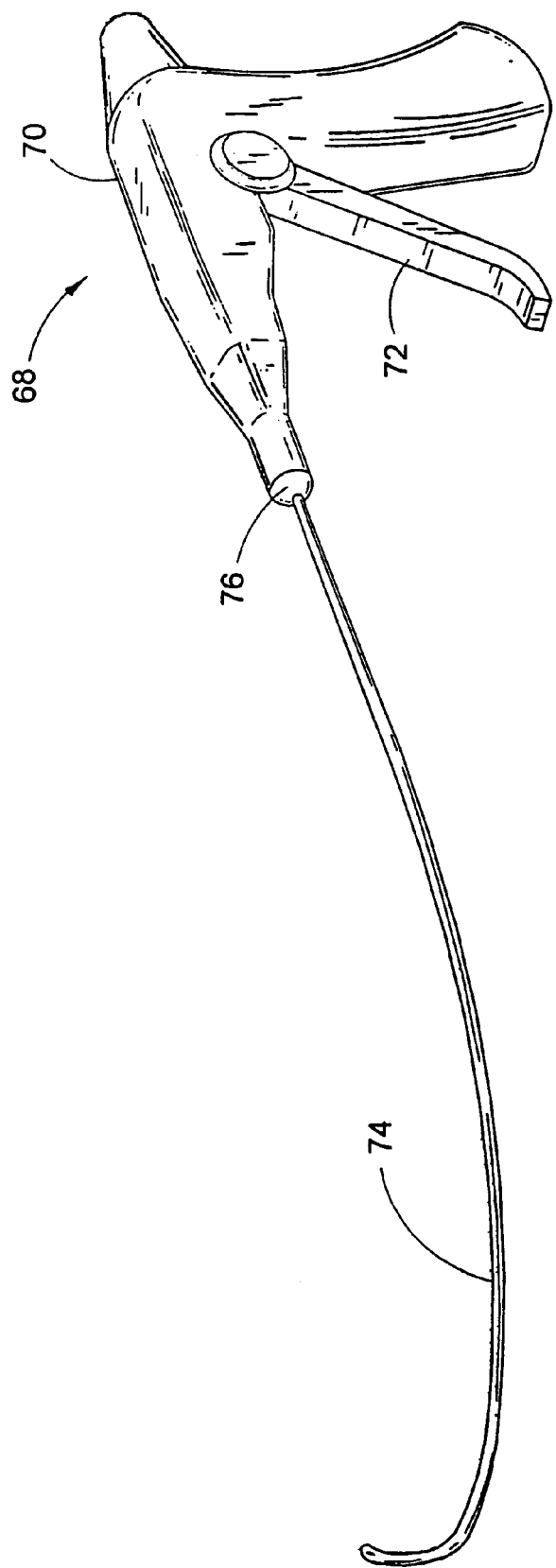
FIG. 26 is a perspective view of an inserter device used to insert a bulkhead stent.
Figure 27A:
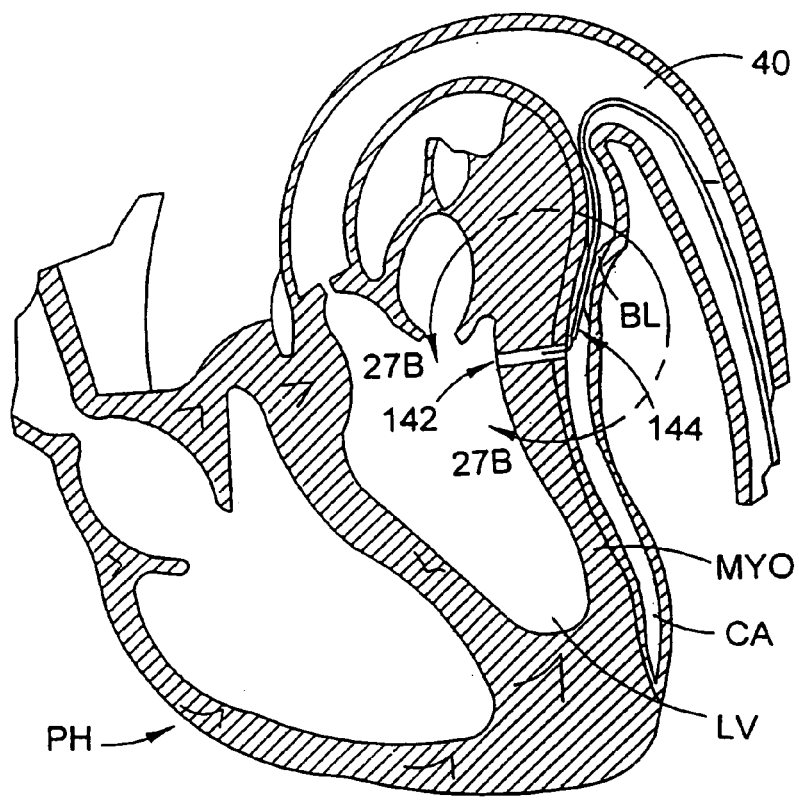
FIG. 27A is a schematic, cross-sectional view of the human heart, showing a catheter used to form a channel through the myocardium and into the left ventricle inserted into the coronary artery.
Figure 27B:
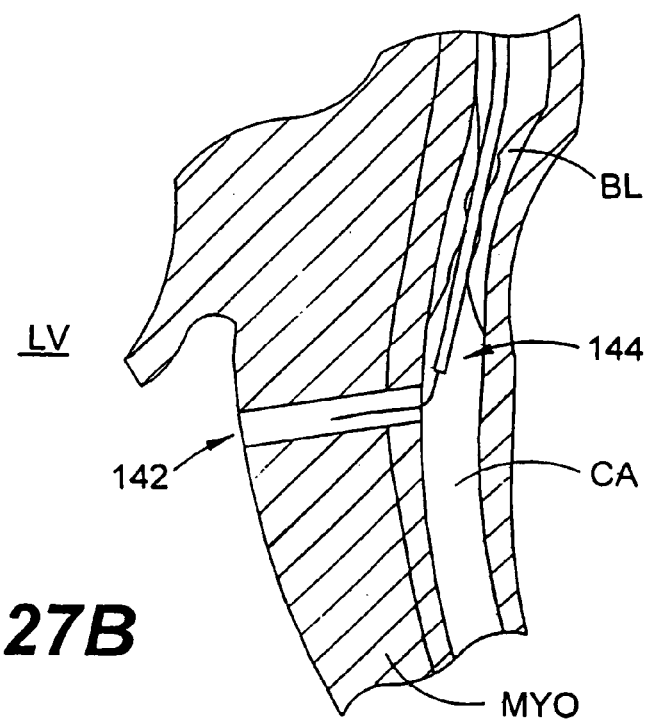
FIG. 27B is an enlarged view of the distal end of the catheter and the channel through the myocardium in FIG. 27A.

FIG. 26 illustrates an inserter device or handle 68 that may be used in deploying the bulkhead stent 50 into the myocardium. The inserter handle 68 preferably comprises a gun 70 with a trigger 72, and a wire 74 extending from a nozzle 76. The rings 64 (not shown) of the bulkhead stent 50 are preferably loaded onto the wire 74, and may be deployed into the myocardium preferably one at a time by pressing the trigger 72.

Screw Stent

Figure 28:
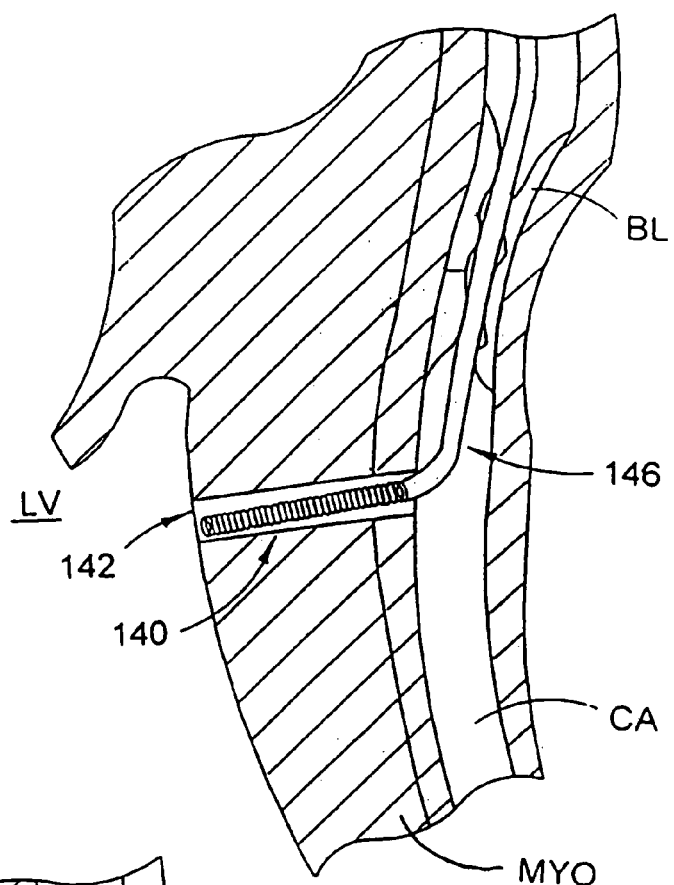
FIG. 28 is a schematic, cross-sectional view of a stent delivery catheter positioned inside the channel formed in the myocardium.
Figure 29:
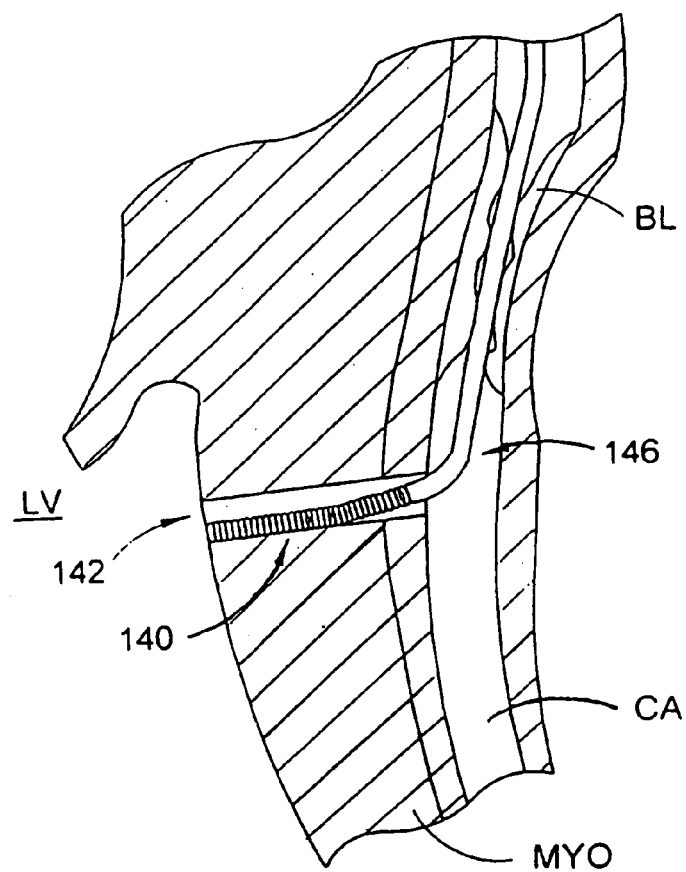
FIG. 29 is a schematic, partial cross-sectional view of a self-expanding spring stent being positioned in the channel formed in the myocardium.
Figure 30:
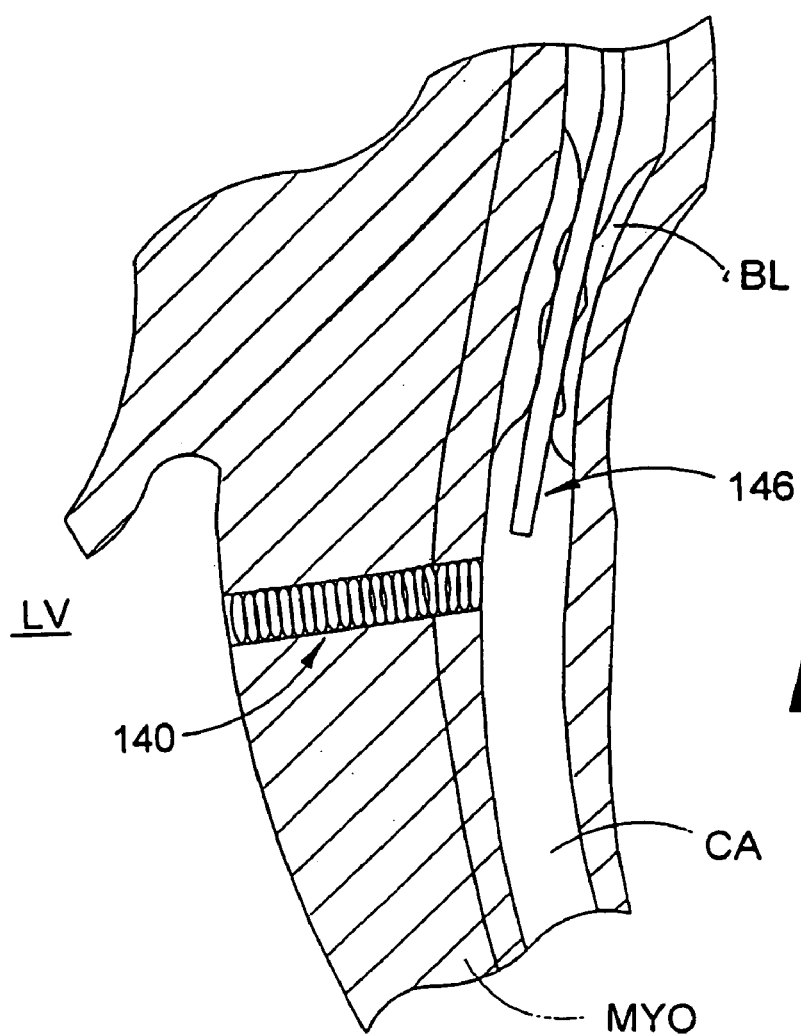
FIG. 30 is a schematic, partial cross-sectional view of the self-expanding stent deployed within the myocardium.

FIGS. 27-30 illustrate another embodiment of the present invention. Here, a self-expanding spring or screw stent 140 is delivered into the myocardium MYO. As illustrated in FIG. 27A, a channel 142 through the wall of the myocardium MYO is first created, as described above, using a device 144 delivered through the aorta AO and coronary artery CA. The channel 142 travels from the coronary artery CA through the myocardium MYO and into the left ventricle LV as shown in FIG. 27B. The distal end of the stent delivery catheter 146 bearing the stent 140 is then positioned within the channel 142, as shown in FIG. 28. Preferably, the position of the distal end of the delivery catheter 146 is checked radiographically, to ensure proper positioning. Next, as illustrated in FIG. 29, the self-expanding spring stent 140 is delivered into the channel 142 wall of the myocardium MYO. The stent 140 is cut such that it does not extend past the myocardium MYO and into either the left ventricle LV or the coronary artery CA. Again, the proper positioning and length of the stent 140 is preferably checked radiographically and any necessary adjustments made before the delivery catheter 146 is removed, as shown in FIG. 30.

Stent with Retention Members

Figure 31:
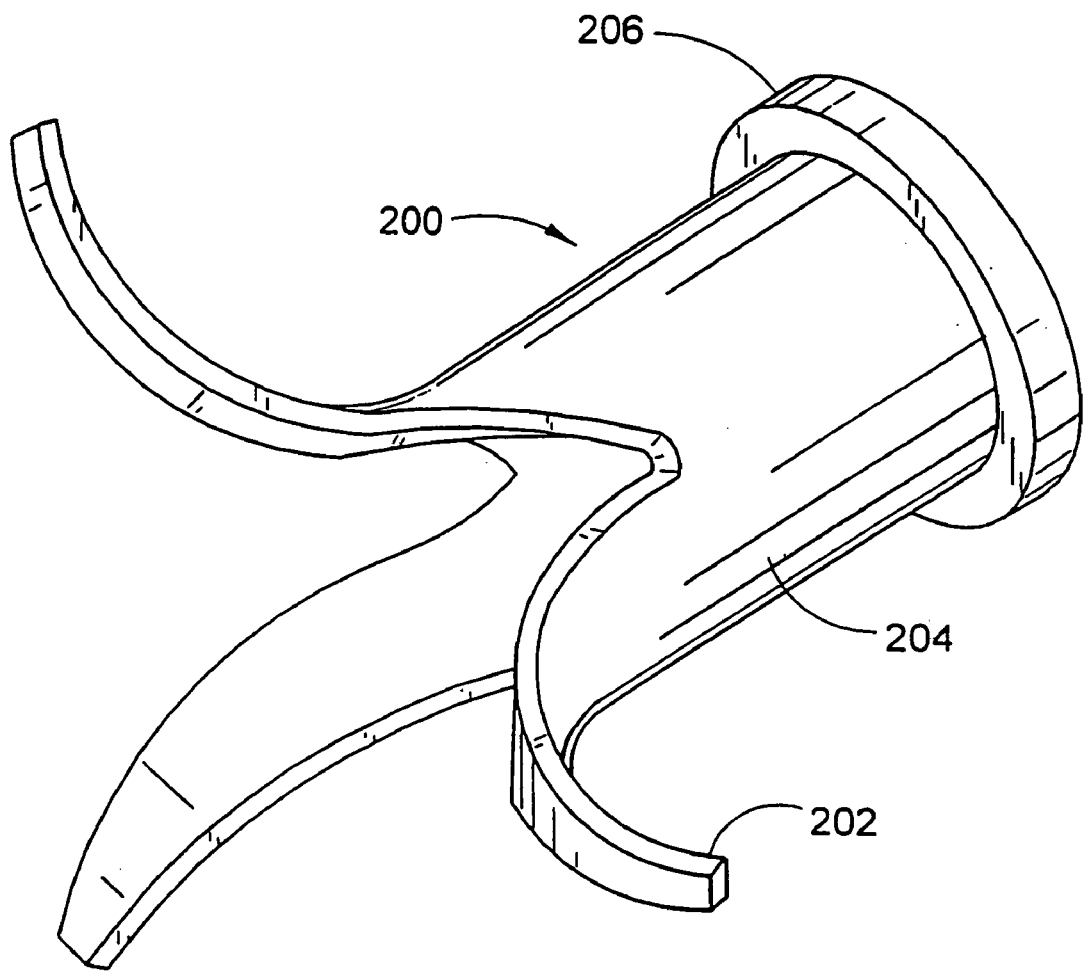
FIG. 31 is a perspective view of another embodiment of a stent having retention members which maintain the position of the stent.

FIG. 31 illustrates another embodiment of the stent 200 having retention members 202. The hollow stent body 204 is held in place in the heart wall by one or more retention members 202 which are deployed after the stent 200 is properly positioned, as described above. FIG. 31 shows the retention members 202 in their deployed position. A flange 206 acts to seal the opening in the coronary artery, while the retention members 202 reside in the myocardium, helping to anchor the stent 200 in place.

Distal Top Shunts

Figure 32:
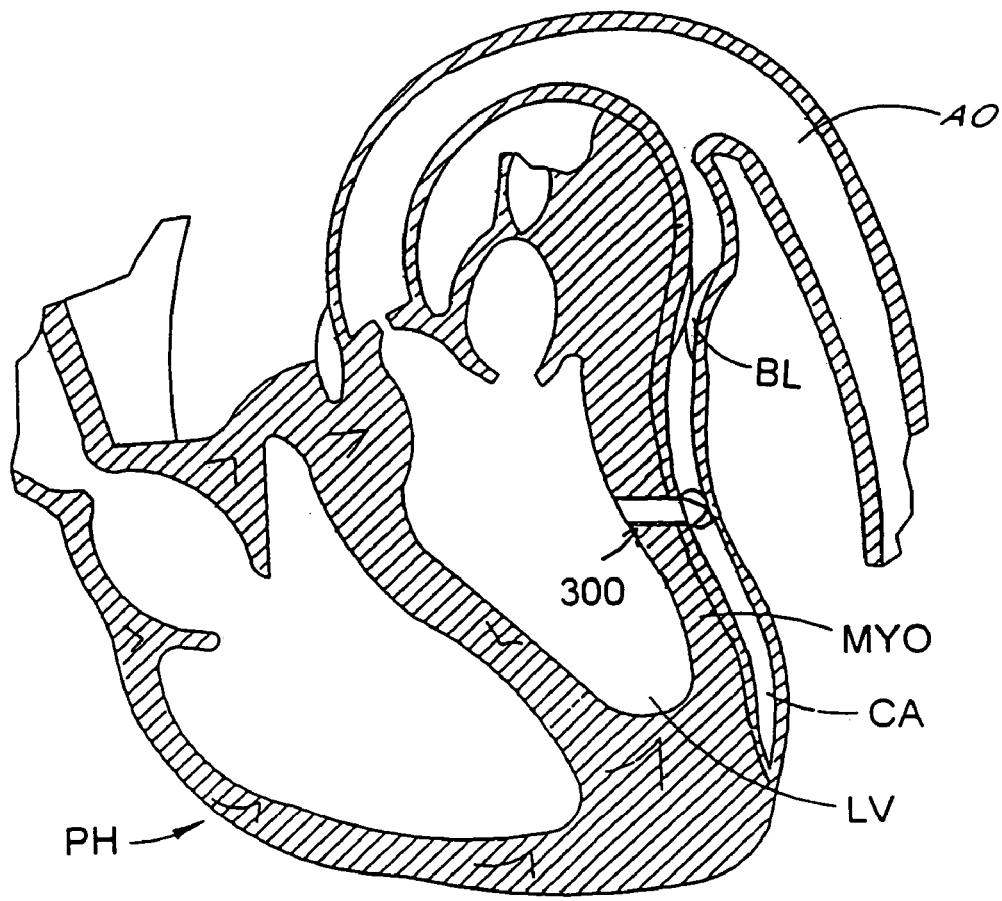
FIG. 32 is a schematic, cross-sectional view of a human heart, showing a conduit in the myocardium of the heart for forming a bypass shunt between the left ventricle and a coronary artery.

In another embodiment, as illustrated in FIG. 32, a coronary artery bypass is accomplished by disposing a left ventricular conduit 300 in a heart wall or myocardium MYO of a patient's heart PH. The conduit 300 preferably extends from the left ventricle LV of heart PH to a clogged coronary artery CA at a point downstream of a blockage BL. Conduit 300 is preferably made of a biocompatible material such as stainless steel or nitinol, although other materials such as Ti, Ti alloys, Ni alloys, Co alloys and biocompatible polymers may also be used. The conduit 300 may also be coated. The conduits described herein are further characterized by a distal top that is preferably collapsible into a first configuration and expandable into a second configuration. The collapsible and expandable characteristics of the distal top may be accomplished by using a shape memory alloy or superelastic material.

Figure 33A:
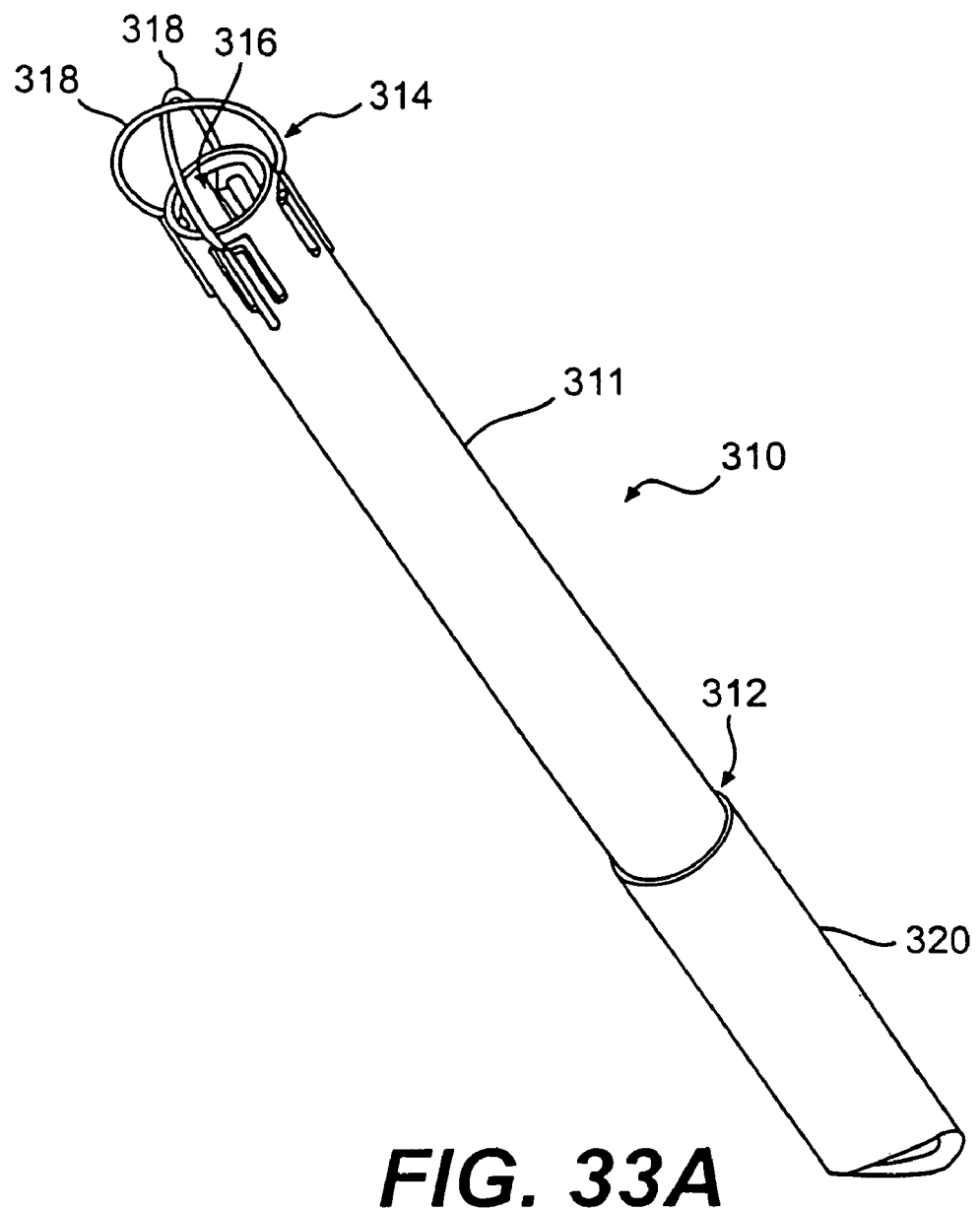
FIG. 33A is a side view of a wire top shunt according to one embodiment of the present invention.

FIG. 33A illustrates a wire top shunt 300 according to one embodiment of the present invention. The shunt 300 preferably comprises an elongate tubular body 311, preferably made of NiTi, having a proximal end 312 and a distal end 314 and a lumen 316 extending therethrough. The distal end 314 corresponds to the end that opens into the coronary artery CA. The proximal end 312 as shown is joined to the distal end of second tube 320, which is preferably made of stainless steel. In one embodiment, the second tube 320 may be a sheath over the tube 312. In the embodiment shown, the shunt 310 comprises both the tubular body 311 and the tube 320, with the proximal end of tube 320 (not shown) opening into the left ventricle. The diameter change from tube 312 to tube 320 allows for a smooth transition from the unsheathed section of the shunt to the sheathed section. The step between the two tubes also provides a mechanical stop for the shunt which is used to transmit axial force from the sheathed section to the shunt during insertion.

Wire loops 318 are preferably attached to the distal end 314 to form the distal top. The wire loops preferably form a generally ball-shaped configuration, with the diameter of the ball corresponding approximately with the diameter of the artery. When implanted, the wire loops 318 are preferably located in the coronary artery CA to hold the shunt therein. The wire loops 318 preferably expand beyond the diameter of the tubular body. Therefore, these loops are preferably collapsible such that they can be inserted into a delivery tube, as described below.

Figure 33B:
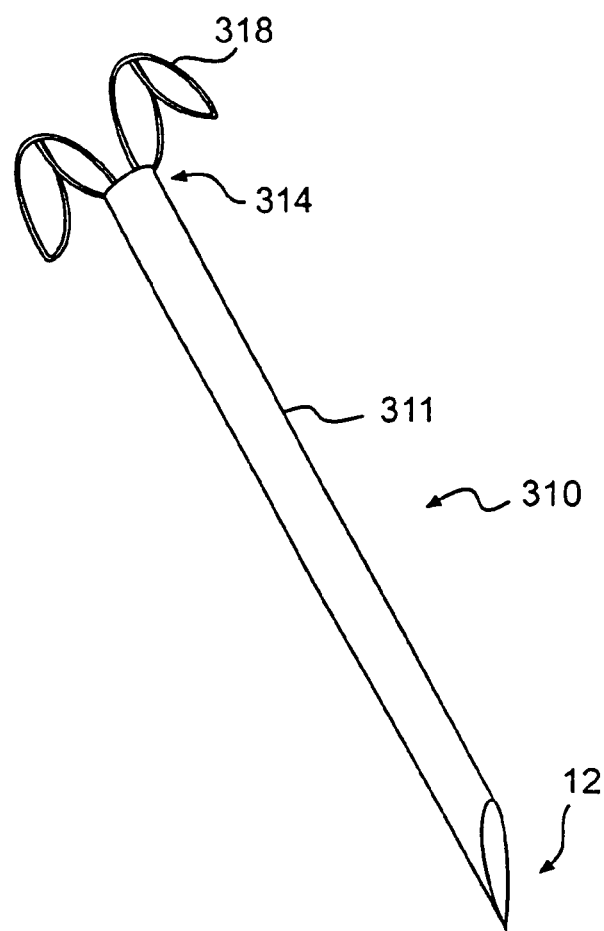
FIG. 33B is a side view of a wire top shunt according to another embodiment of the present invention.
Figure 33C:
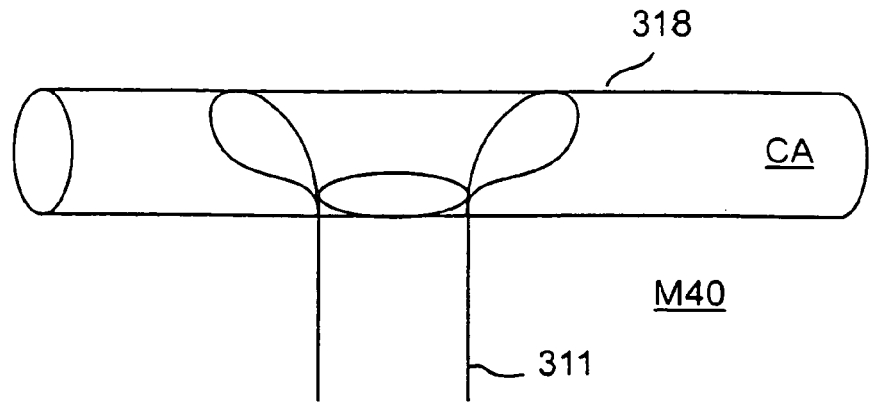
FIGS. 33C-33F are schematic side views of wire top shunts inserted into a patient's coronary artery.
Figure 33D:
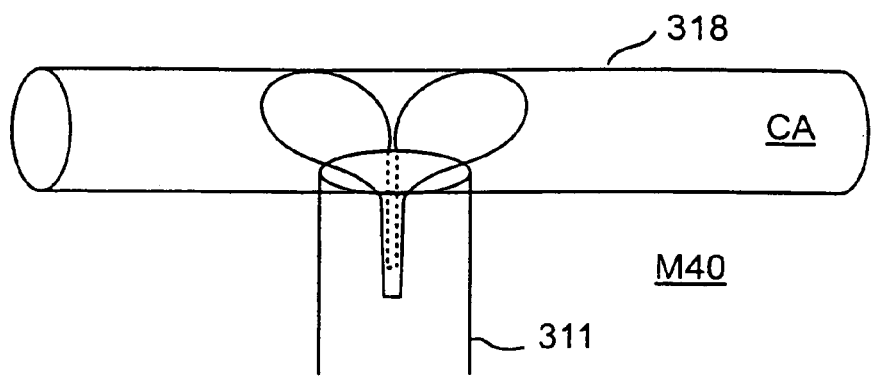
Figure 33E:
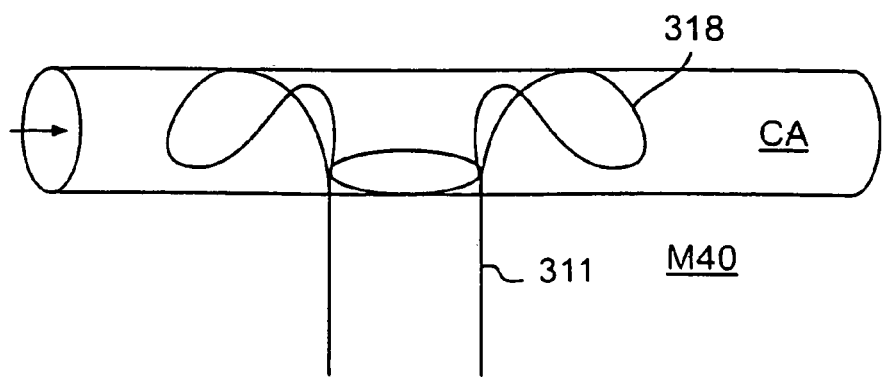
Figure 33F:
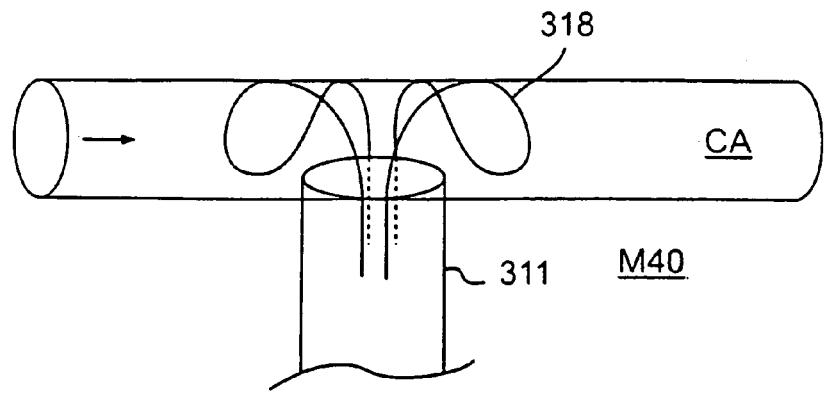

Although FIG. 33A illustrates a design with two loops, it will be appreciated that multiple designs with different numbers of loops and other configurations are possible. Moreover, loops having different shapes, such as hoops, arches, etc., are also contemplated. Furthermore, wires of different sizes may be used. The wire loops 318 and the tubular body 311 may also be integrally formed from a single piece of material and laser cut into the desired configuration. FIG. 33B illustrates another embodiment having folded down loops 318. In this embodiment the shunt 310 has a proximal end 312 which itself opens into the left ventricle when implanted. The proximal end 312 is pointed to assist in inserting the shunt 310 through the heart wall, as described below.

FIGS. 33C-33F illustrate different embodiments of a loop top shunt implanted in a patient. More particularly, the proximal end (not shown) of the conduit preferably extends into the left ventricle, and the distal end having loops 318 extends into the coronary artery. The loops 318 of each of these embodiments are preferably sized to open against the walls of the coronary artery CA, as shown.

Figure 33G:
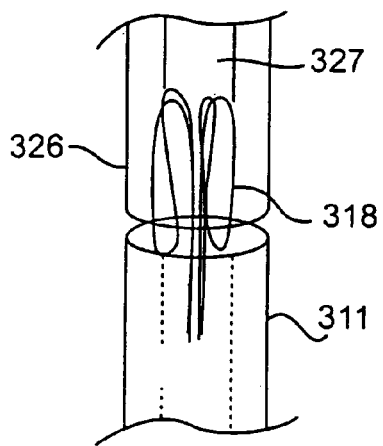
FIGS. 33G-33I are schematic side views of a delivery sequence for inserting a wire top shunt.
Figure 33H:
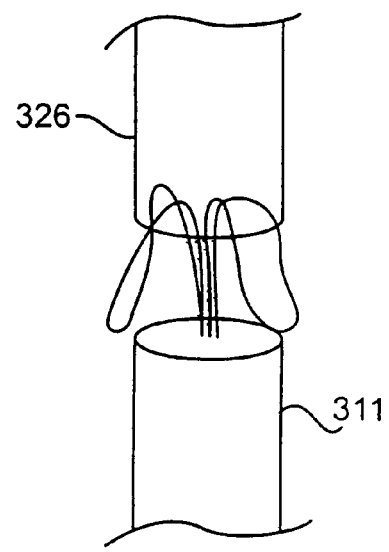
Figure 33I:
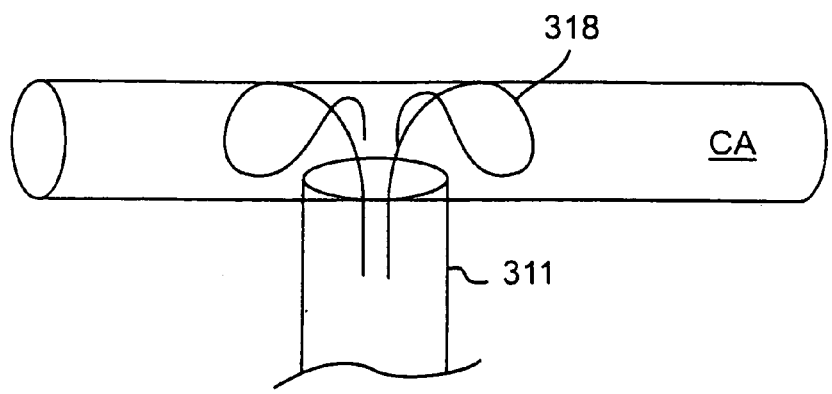

FIGS. 33G-33I illustrate one preferred delivery sequence of a shunt having wire loops 318. It will be appreciated that this delivery method can be applied to other types of shunts, such as the shunts described below. As shown in FIG. 33G, a delivery sheath 326 is placed over the loops 318 to restrain the loops into a collapsed configuration. An optional stylet 327 may also be used to restrain the loops. In this configuration the shunt is implanted into a heart wall, with the loops 318 (located within the sheath 326) being positioned in a coronary artery CA. As shown in FIG. 33H, the sheath 326 is removed, allowing the loops 318 to expand outward. As shown in FIG. 33I, when the sheath 326 is fully removed, the loops 318 assume an expanded configuration against the walls of the coronary artery CA.

Figure 34A:
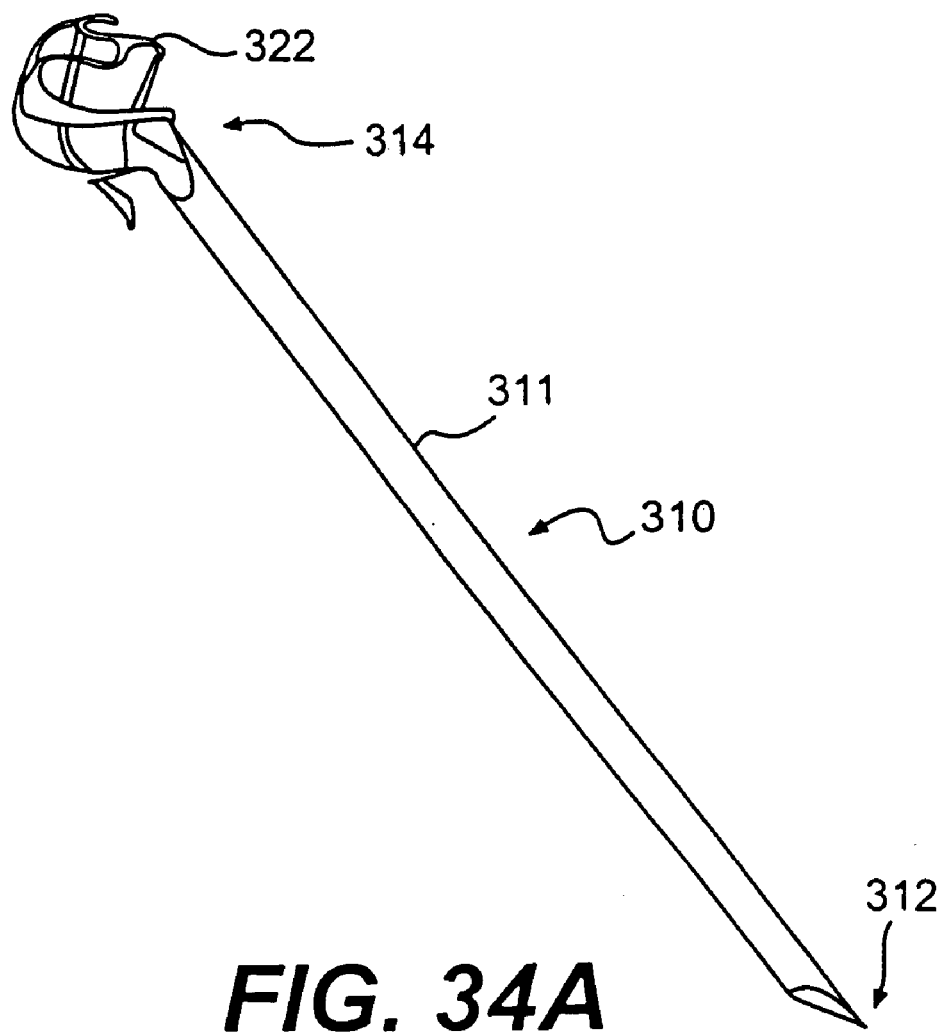
FIG. 34A is a side view of a wire top shunt according to another embodiment of the present invention.
Figure 34B:
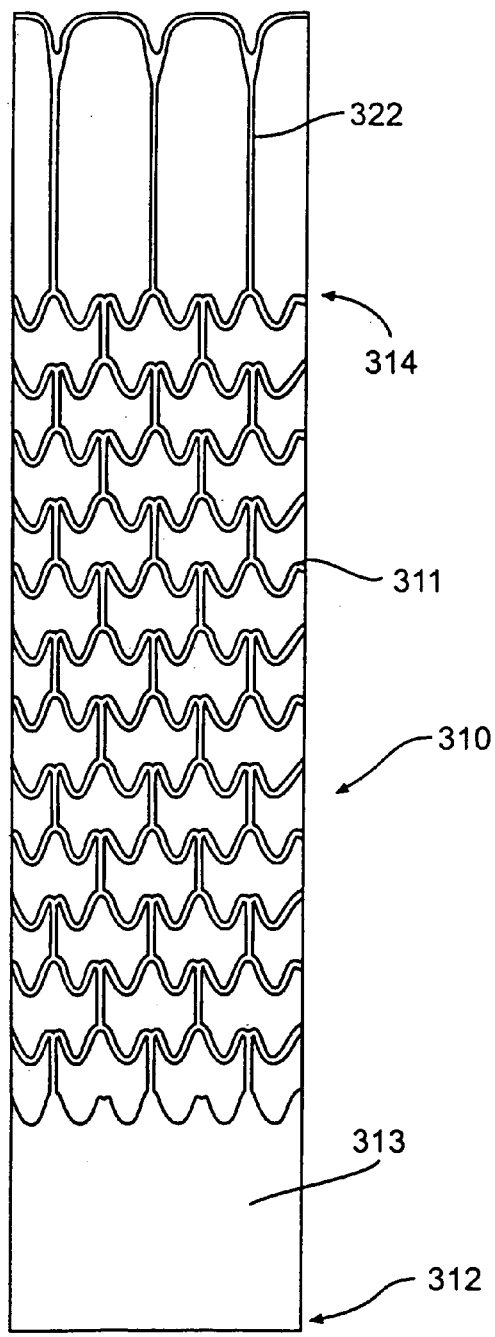
FIG. 34B is a side view of a ball top shunt according to one embodiment of the present invention, the shunt being shown laid out flat.
Figure 34C:
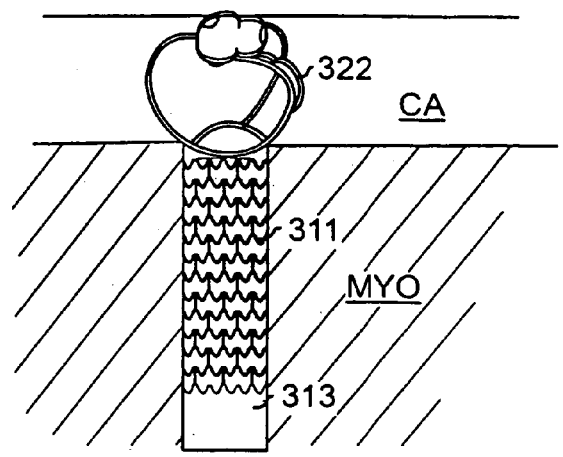
FIG. 34C is a side view of the ball top shunt of FIG. 34B, shown implanted in a patient.
Figure 34D:
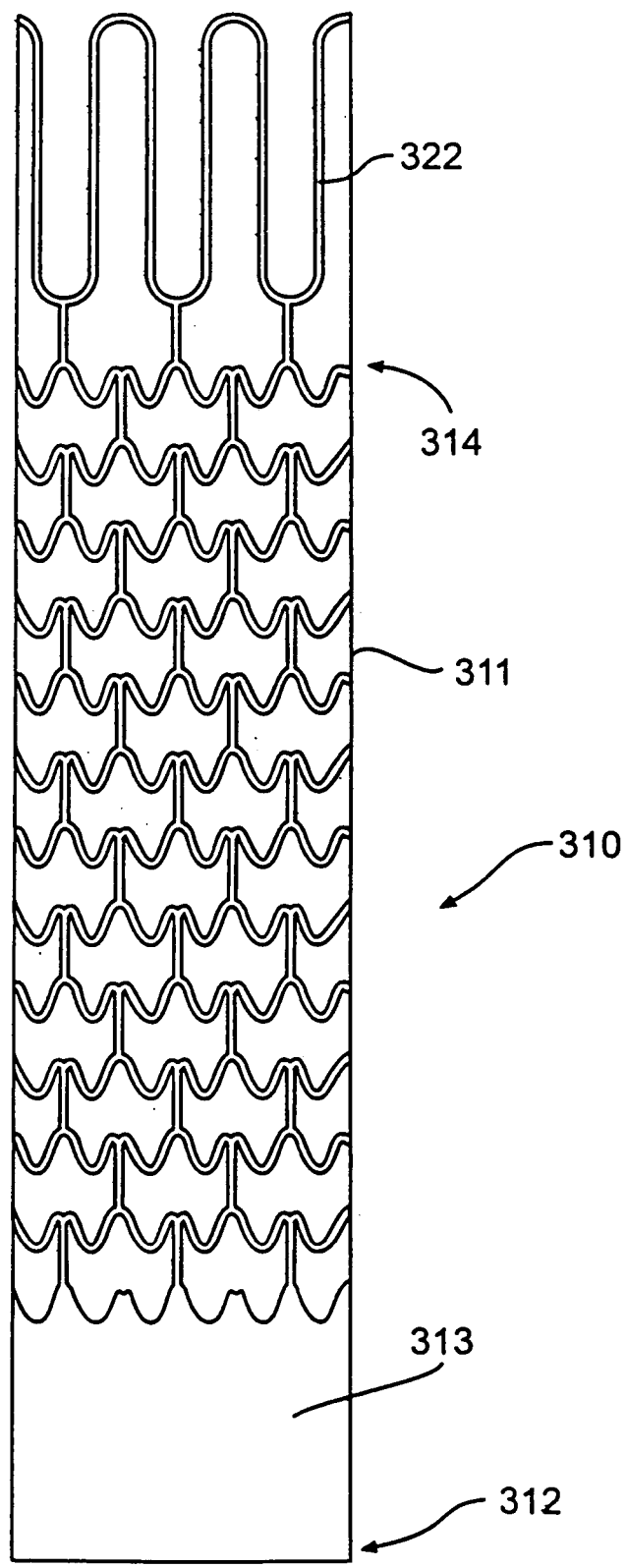
FIG. 34D is a side view of a ball top shunt according to another embodiment of the present invention, the shunt being shown laid out flat.
Figure 34E:
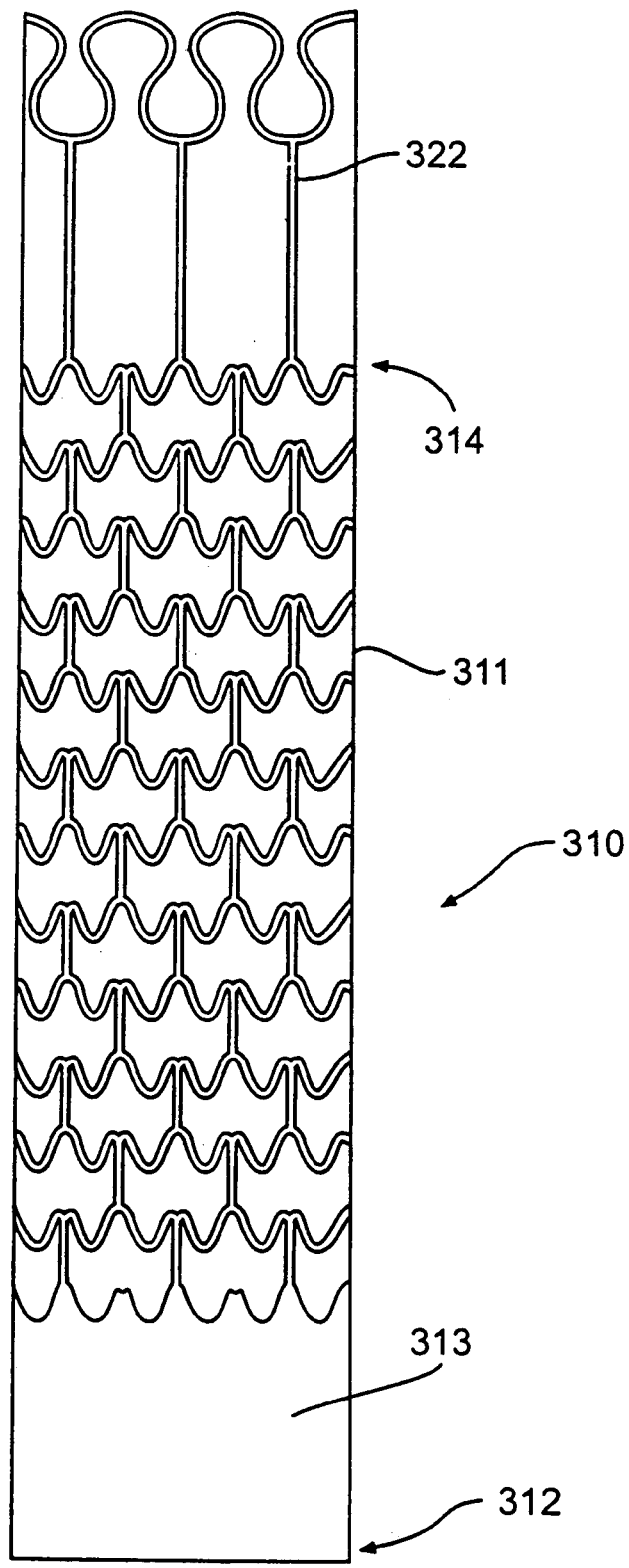
FIG. 34E is a side view of a ball top shunt according to another embodiment of the present invention, the shunt being shown in its preassembly configuration.

FIG. 34A illustrates another embodiment of a shunt 310. In this embodiment, the tubular body 311 is preferably made of NiTi, and preferably has a proximal end 312 which itself opens into the left ventricle when implanted. The shunt 310 of FIG. 34A has a pointed tip 312 to assist in inserting the shunt 310 through the heart wall, as described below. The distal top in this embodiment is a wire top 322, preferably integrally formed with the tubular body 311, and is to be implanted into the coronary artery CA. The wire top 322 preferably comprises a plurality of wire segments that form generally a ball shape. The shape and size of the ball can be varied to conform to a range of artery sizes. Like the embodiment of FIGS. 32A-32F, the wire top 322 can be collapsed for insertion into the body, and expanded like a stent to position the shunt 310, more particularly the wire top 322, in the artery.

Figure 34H:
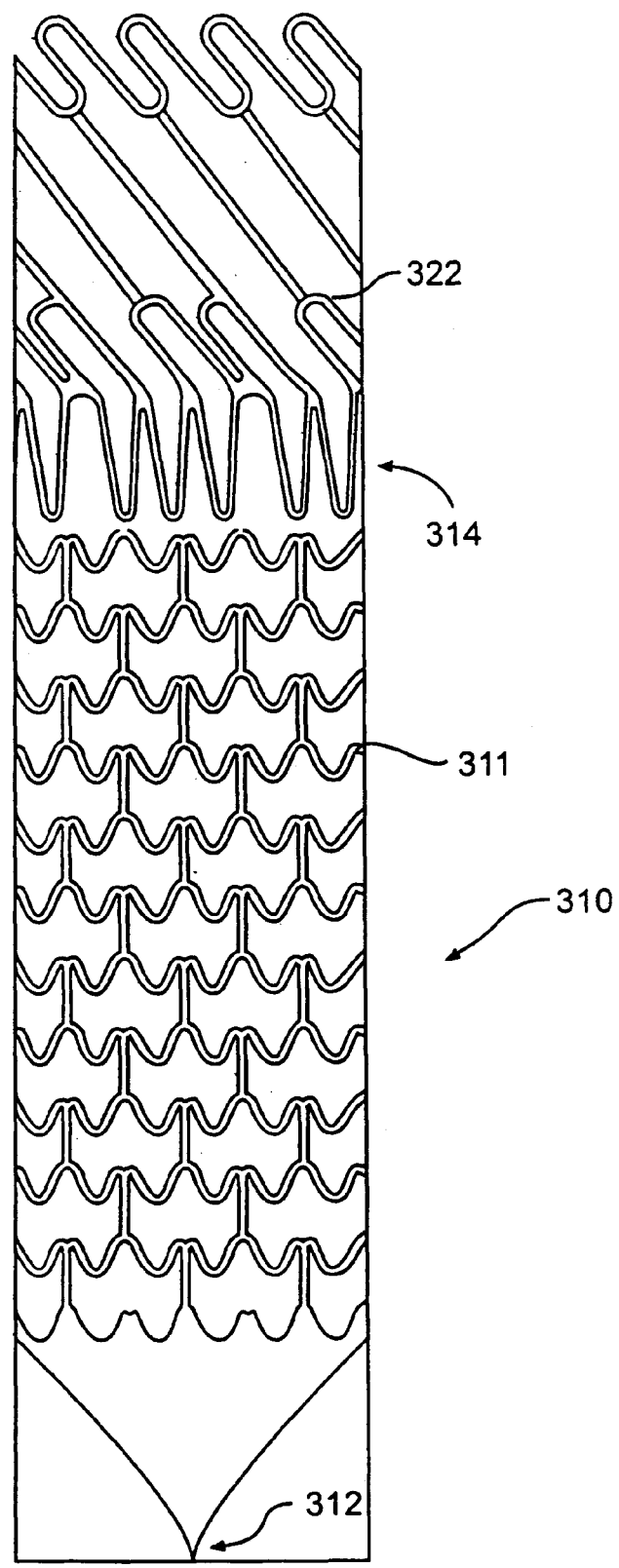
FIG. 34H is a side view of a ball top shunt according to another embodiment of the present invention, the shunt being shown laid out flat.
Figure 34I:
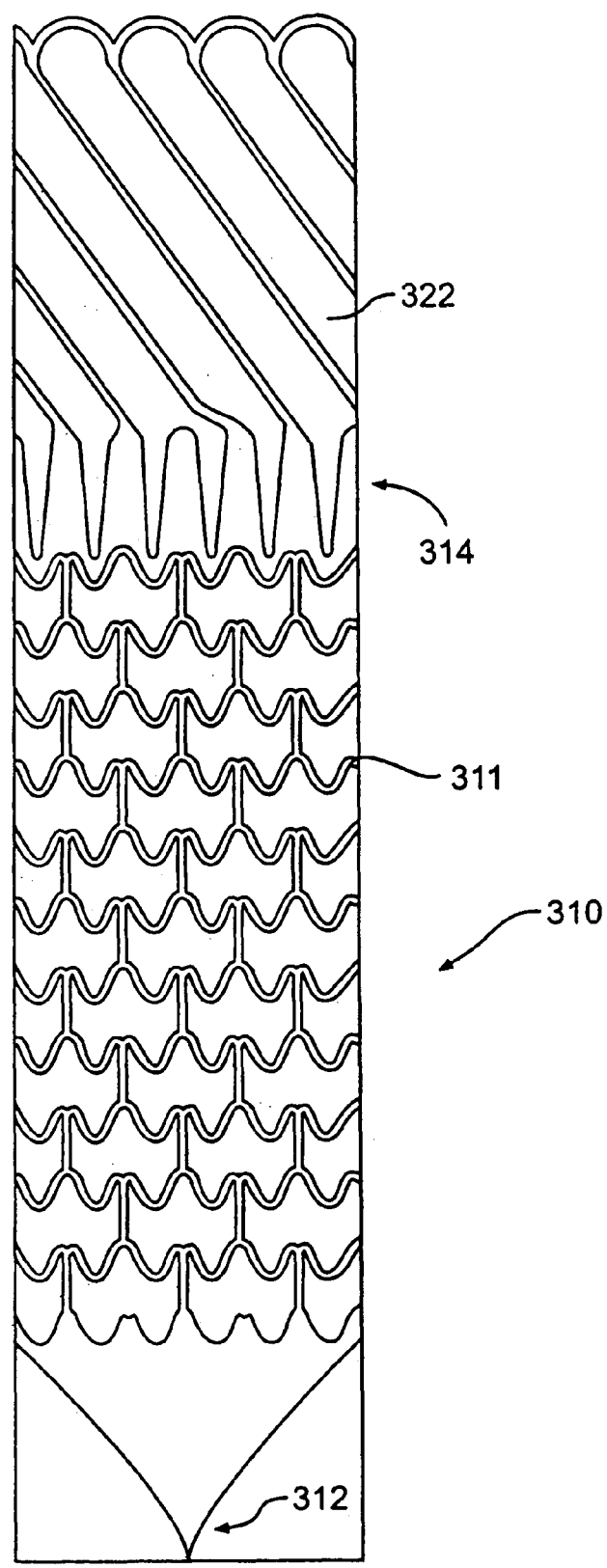
FIG. 34I is a side view of a ball top shunt according to another embodiment of the present invention, the shunt being shown laid out flat.
Figure 34J:
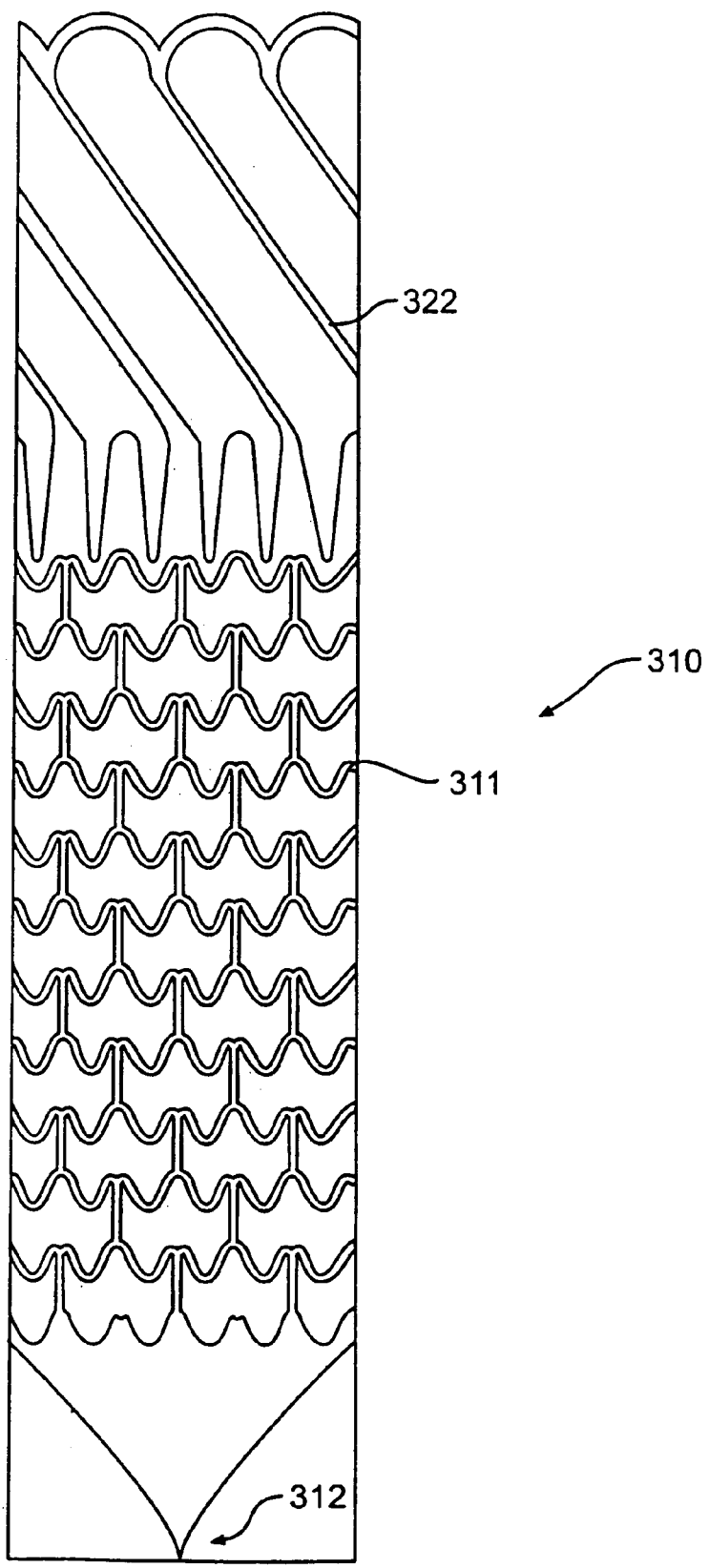
FIG. 34J is a side view of a ball top shunt according to another embodiment of the present invention, the shunt being shown laid out flat.

FIGS. 34B-34I illustrate several other embodiments of ball top stents, particularly showing wire tops 322 having various configurations. Furthermore, the shunts 310 illustrated in FIGS. 34B-34G are formed such that near proximal end 312 the shunt has a solid portion 313, and between solid portion 313 and wire top 322 the shunt 310 substantially comprises a wire frame 311. The wire frame 311 gives the shunt 310 flexibility to bend into curved configurations. This wire frame is preferably laser cut from a solid piece of tubing, though other methods of manufacture may also be used. FIGS. 34H-34J illustrates shunts 310 having substantially solid body constructions, with pointed proximal ends 312.

Figure 34K:
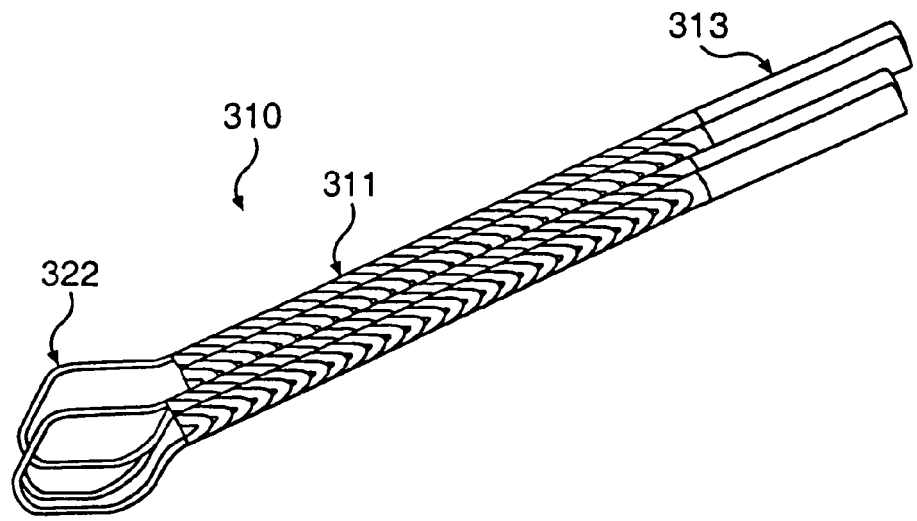
FIG. 34K is a side view of a flexible ball top shunt.
Figure 34L:
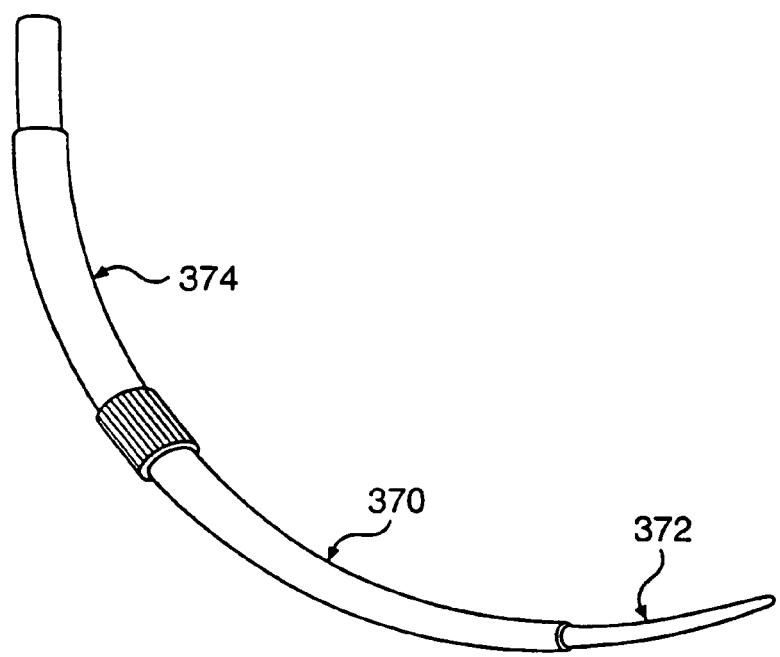
FIG. 34L is a side view of the delivery apparatus for the ball top shunt of FIG. 34K.

FIG. 34K illustrates one embodiment of a shunt 310 having a solid proximal portion 313, a flexible portion 311 and a wire top or ball top 322. FIG. 34L illustrates a delivery system used to delivery the shunt 310 of FIG. 34K. A stylet 372 is inserted through the shunt 310. The stylet 372 as shown may be curved, and because the portion 311 of the shunt is flexible, the shunt 310 also curves. A sleeve 374 extends over the distal top 322 to hold the top in a collapsed configuration. The arrangement as shown in FIG. 34L is inserted into the patient's heart wall, preferably through the coronary artery, through the heart wall and into the left ventricle. The distal top 322 is arranged such that it is located within the coronary artery. The sleeve 374 is removed to expand the distal top 322 in the coronary artery.

Figure 35:
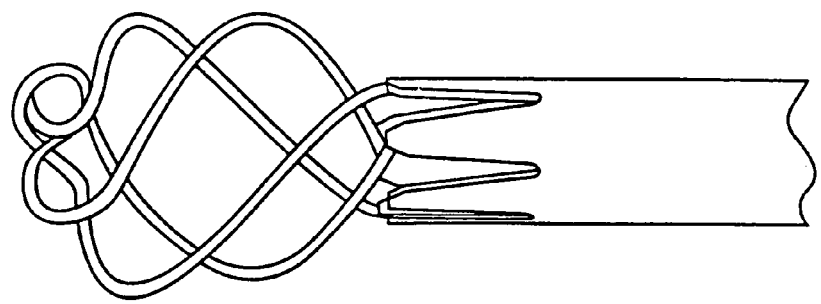
FIG. 35 is a side view of a wire top shunt according to another embodiment of the present invention.
Figure 36:
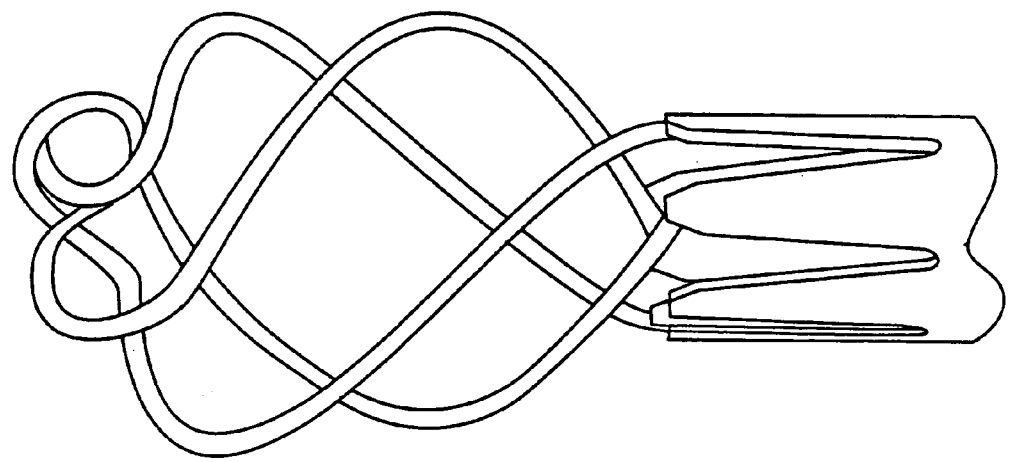
FIG. 36 is an enlarged view of the wire top shunt of FIG. 35.

FIGS. 35 and 36 illustrate enlarged views of a shunt 310 with a wire top 322, where the wire top 322 is preferably integrally formed. As can be seen, the wire top 322 preferably uses a four strut design, wherein the tubular body 311 at the distal end 314 transitions into four wires 324 forming the wire top 322. This embodiment is more preferably referred to as a knub top design.

Figure 37:
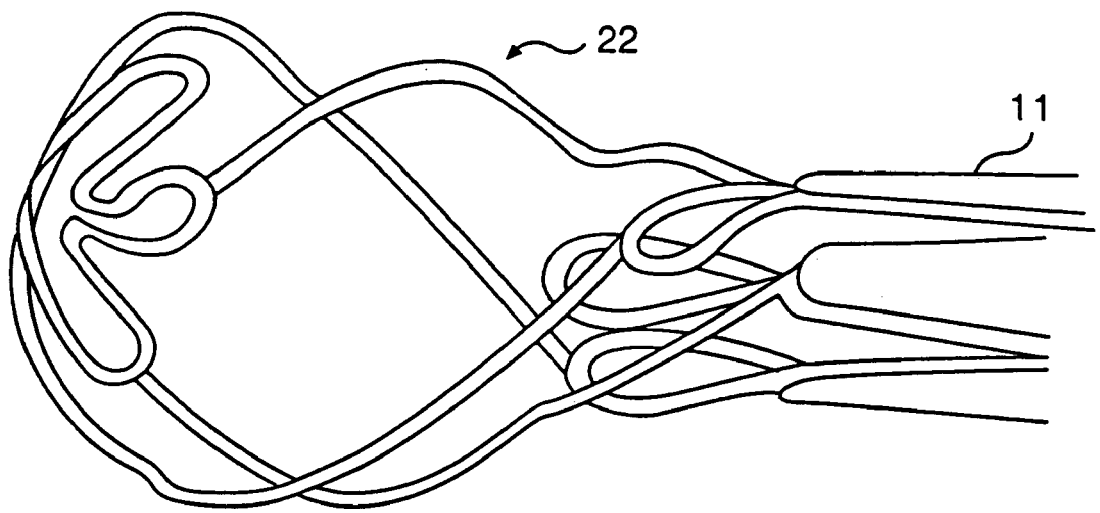
FIG. 37 is a side view of a wire top shunt according to another embodiment of the present invention.
Figure 38:
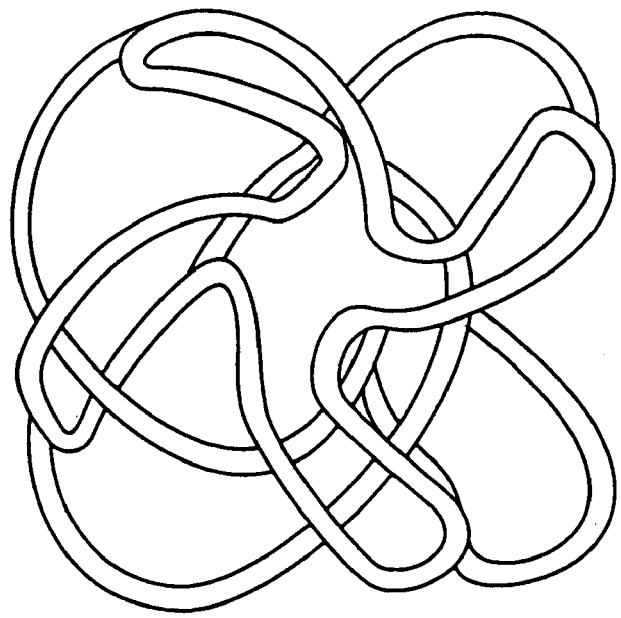
FIG. 38 is a top view of the wire top shunt of FIG. 37.

FIGS. 37 and 38 illustrate another embodiment wherein the shunt of FIGS. 35 and 36 instead have a flat top design.

Figure 39A:
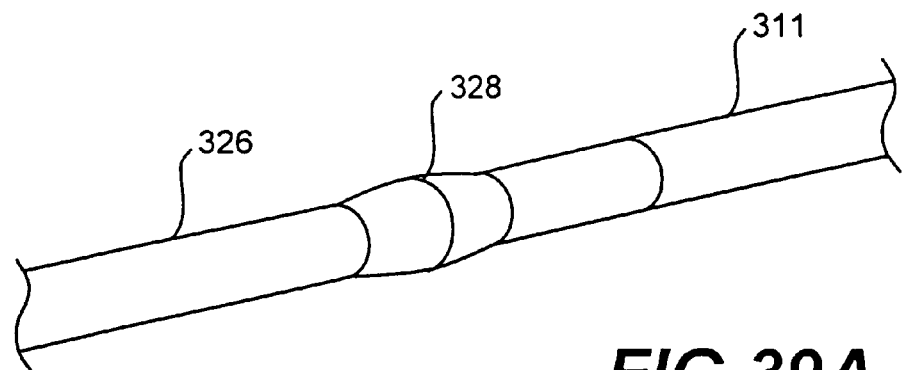
FIGS. 39A-39F are side views showing the deployment sequence of a wire top shunt.
Figure 39B:
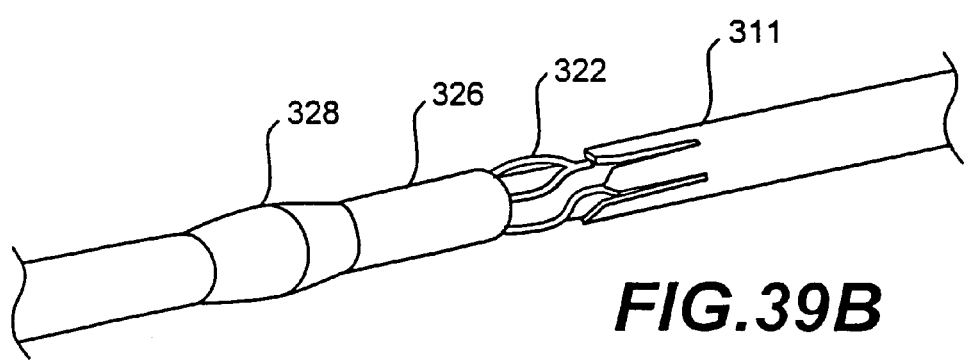
Figure 39C:
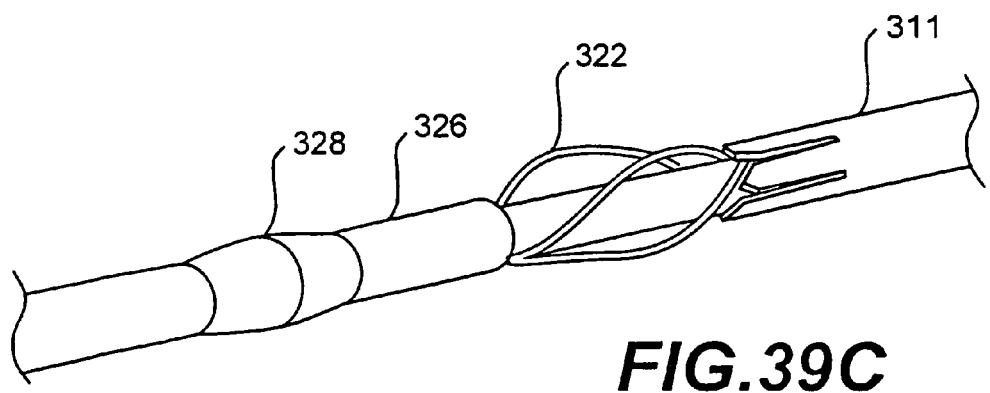
Figure 39D:
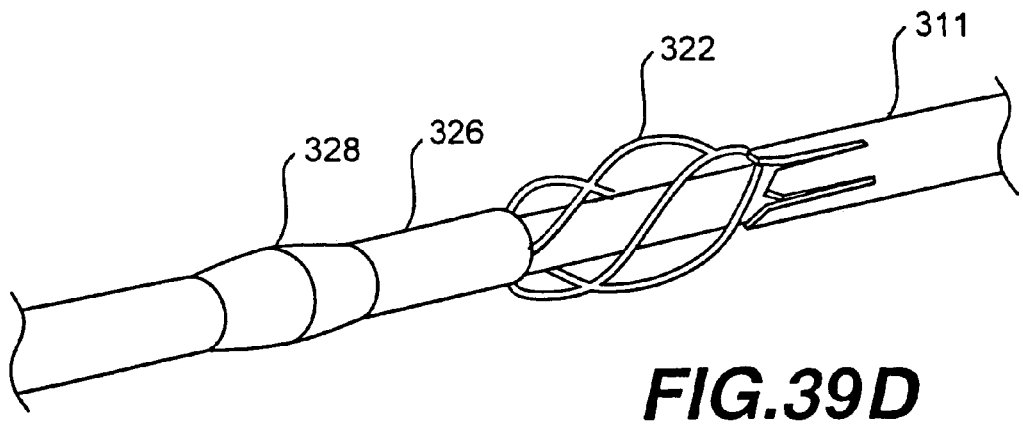
Figure 39E:
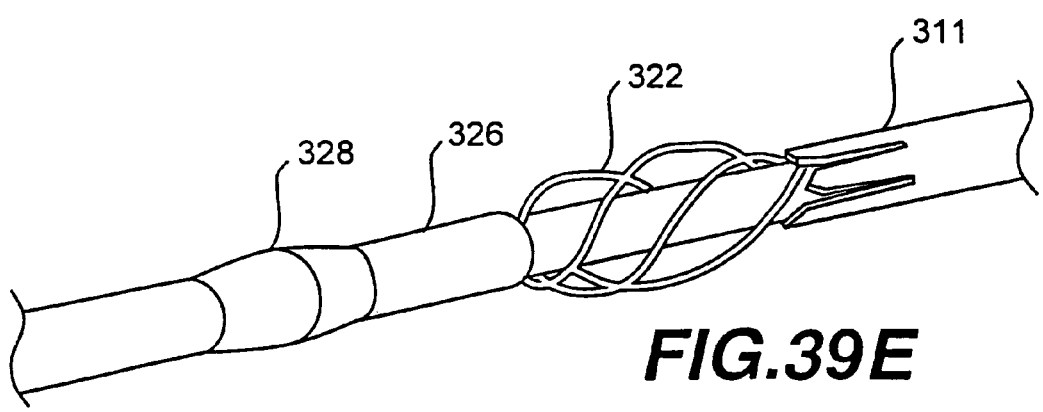
Figure 39F:
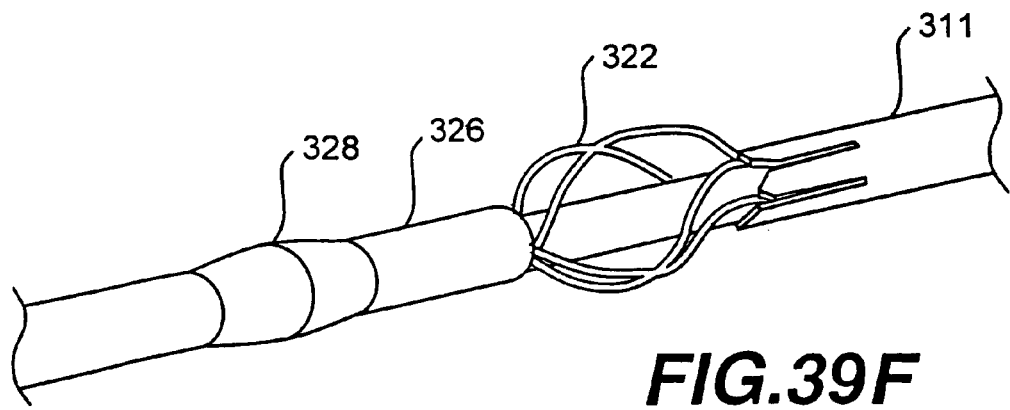

FIGS. 39A-39F illustrate a preferred deployment sequence of a conduit 310 having a wire top 322. The shunt 310 is preferably inserted into the delivery tube 326, distal end first, such that the wire top 322 is inserted into the tube 326 and is collapsed therein. As shown in FIG. 39A, the delivery tube preferably has a bulged region 328 for receiving the wire top 322 when in its collapsed configuration. The bulged region 328 gives the operator tactile feedback for sensing when the sheath is in the proper position for deployment. The arrangement shown in FIG. 39A, in one embodiment, is inserted into the heart with the proximal end of the shunt 310 extending into the left ventricle and the distal end of the shunt extending into the coronary artery. With the shunt 310 in position, the delivery tube is retracted, as shown in FIGS. 39B-39F from the shunt to release the wire top 322 into its expanded configuration in the coronary artery.

Figure 40A:
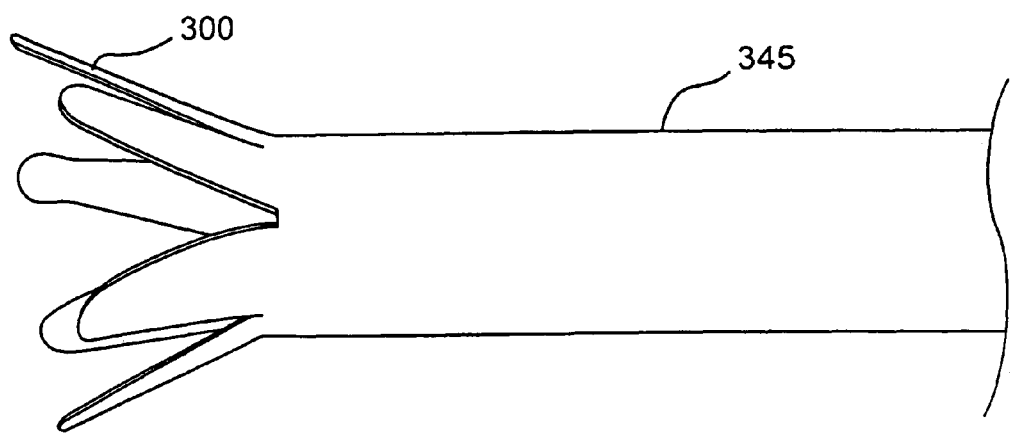
FIG. 40A is a side view of a flare top shunt according to one embodiment of the present invention.

FIG. 40A illustrates another embodiment of a shunt 310 having a flare top 330. The shunt illustrated in FIG. 40A has six flares extending from distal end 314 and integrally formed therewith. It will be appreciated that fewer or more flares may be provided, and that these flares may extend away from the shunt body 311 at various angles to hold the shunt within the coronary artery. These flares are preferably collapsible to allow the shunt to be inserted into a delivery tube such as described above. FIGS. 40B and 40C illustrate a flip-down shunt having sections 332 which fold down when implanted in a patient to anchor the shunt to the artery CA. This shunt 310, as illustrated, has a wire portion 311 and a solid portion 313.

Figure 41:
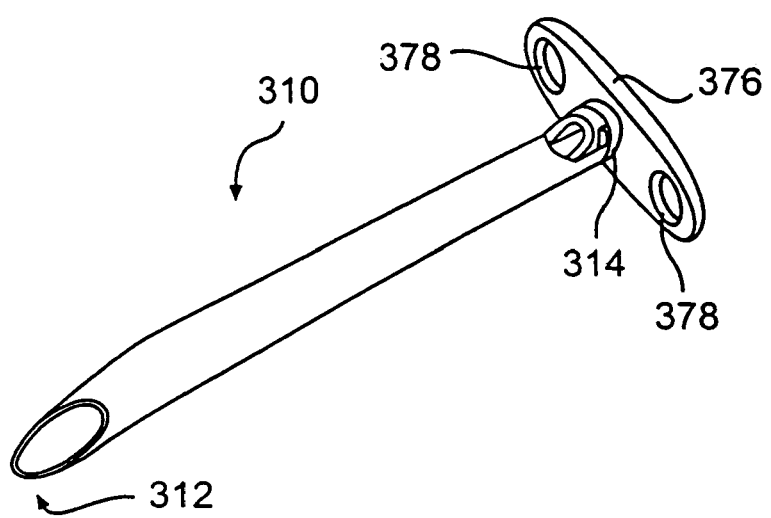
FIG. 41 is a side view of a shunt with a T-flange.

FIG. 41 illustrates another embodiment of a shunt 310. The shunt 310 has a proximal end 312 and a distal end 314, the proximal end preferably having an opening for receiving blood from the left ventricle. The distal end also has an opening for delivering blood from the left ventricle to the coronary artery. The shunt 310 shown in FIG. 41 preferably has a T-flange 376 at the distal end. When implanted, this T-flange preferably is positioned on the outside of the heart, and holes 378 are used to suture the device to the heart wall.

Hinged Conduit

Figure 42:
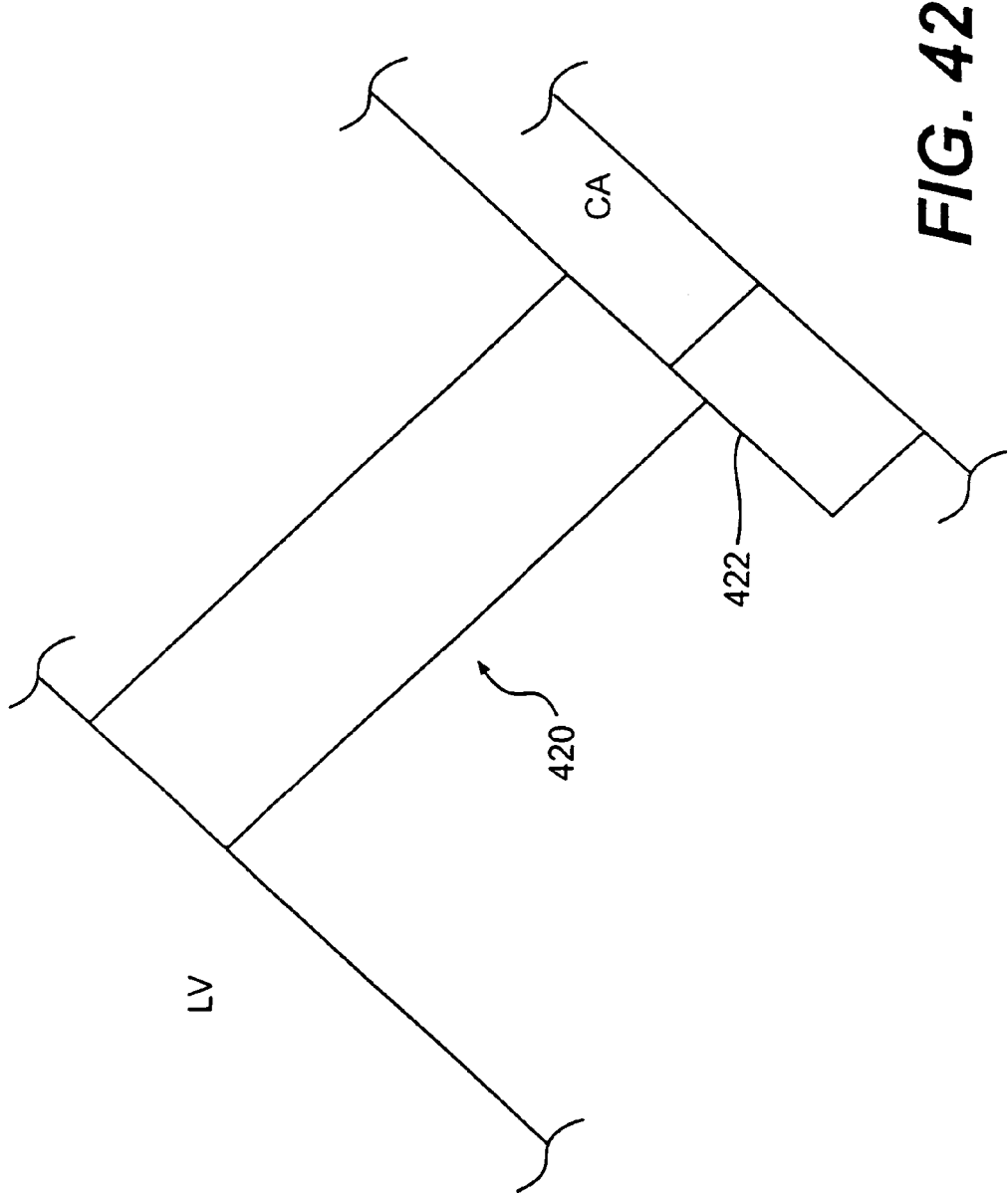
FIG. 42 is a schematic view of a hinged conduit.

Additional embodiments include conduits which are engaged and aligned with the left ventricle and the coronary artery in the patient's heart. FIG. 42 illustrates a conduit 420 for connecting the left ventricle LV to the coronary artery CA. The conduit 420 comprises a solid tube that has a cut section 422 that can be bent over to align with the artery CA.

Figure 43:
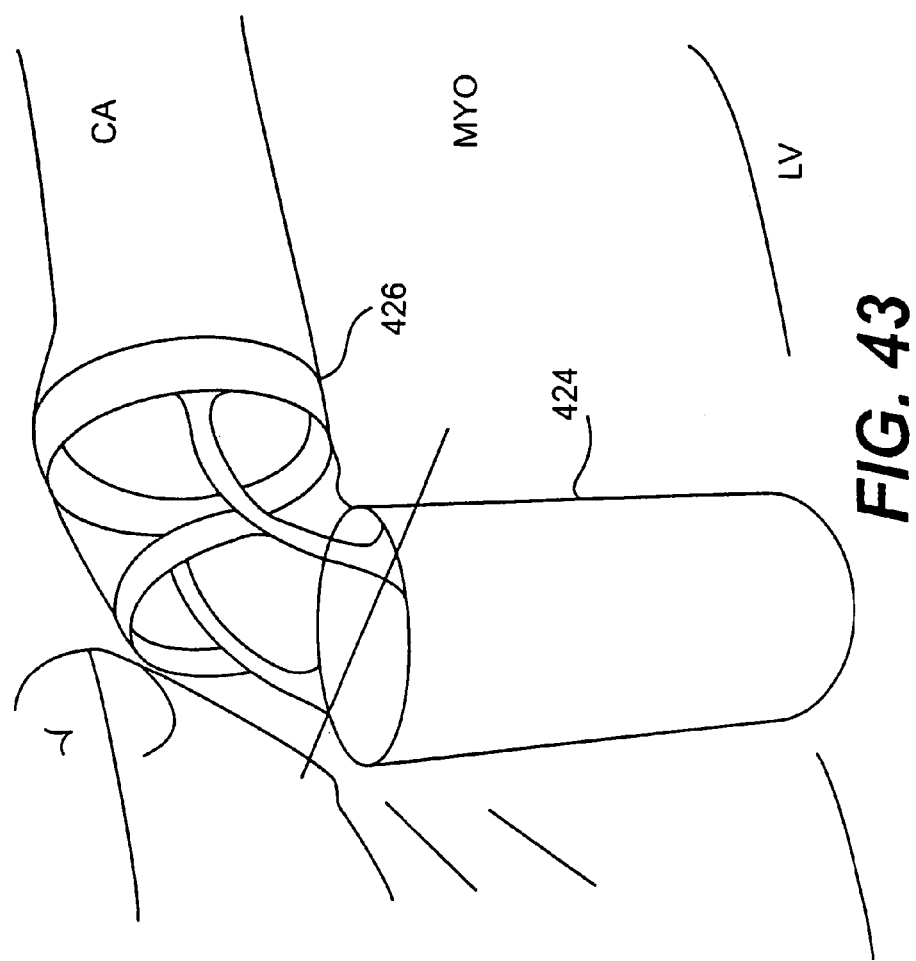
FIG. 43 is a schematic view of another embodiment of a hinged conduit.

FIG. 43 illustrates a conduit 424 similar to the conduit of FIG. 42, which is more preferably a nitinol stent having a short hinged section 426 to align with the coronary artery.

Bell-Shape Conduit

Figure 44A:
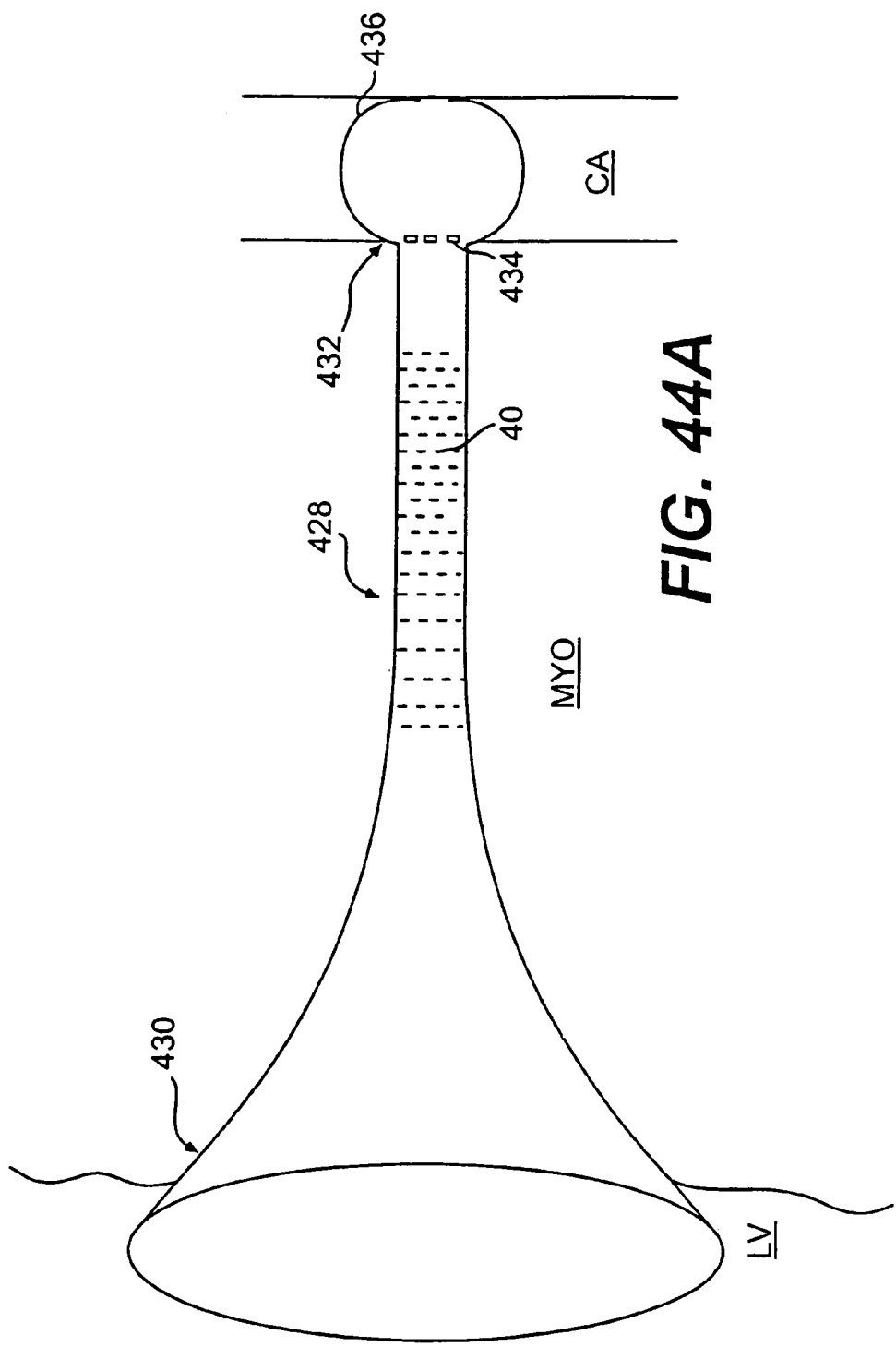
FIG. 44A is a schematic side view of a bell shape stent having a web flange and an axially expandable region.

FIGS. 44A and 44B illustrate an alternate embodiment of a conduit 428 between the left ventricle and coronary artery which is preferably a nitinol stent. The proximal end 430 of the stent opening into the left ventricle preferably is heat set to have a bell shape to hold to the interior heart wall and to introduce flow. The distal end 432 preferably has small heat set fingers 434 which extend outward to anchor the stent against the interior wall of the coronary artery. A web flange 436 on the distal end 432 preferably comprises two or more rings which, when placed in the heart, open in the coronary artery to position the conduit while allowing blood flow. These rings are preferably shaped to extend outward in a curved configuration as shown in FIG. 44A when deployed. Between the proximal and distal ends is an axially expandable region 438, provided by slots 440 cut in the region.

FIG. 44C illustrates a stylet 442 used for inserting a conduit 428 having the web flange 436 shown in FIGS. 44A and 44B. More particularly, the stylet 442 is inserted through the rings of the web flange 436 to bring the rings together or closed for insertion. Removal of the stylet 442 after the conduit 428 is placed in the heart allows the rings to expand outward to the shape shown in FIGS. 44A and 44B.

Conduit Having Annular Grooves

Figure 45:
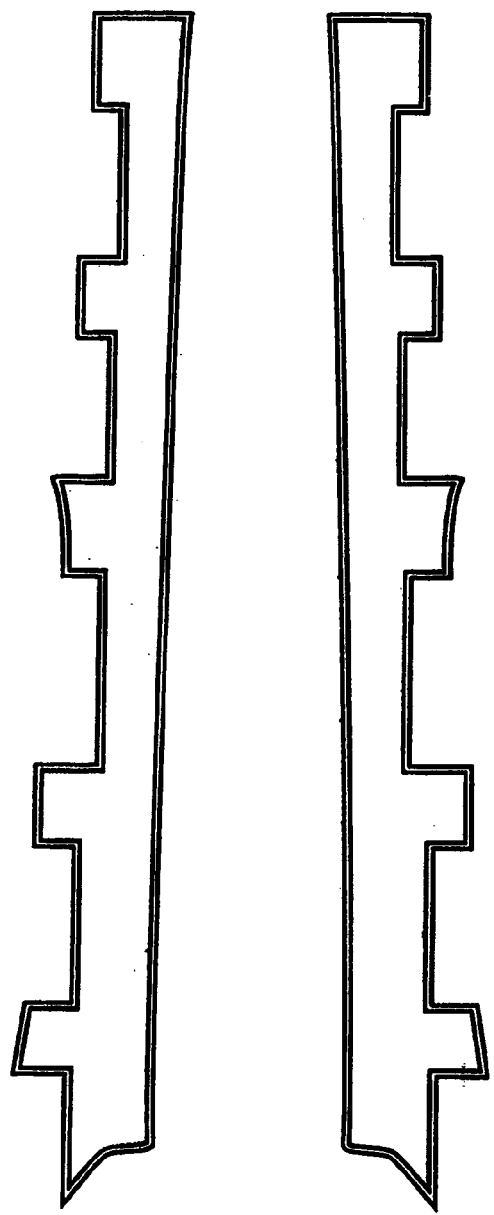
FIG. 45 is a schematic side view of a conduit having annular grooves.

FIG. 45 illustrates an embodiment where the conduit is provided with annular grooves. Grooves may also be provided longitudinally along the conduit. The raised or protruding portions on the outer surface of the conduit are imbedded into the heart wall to anchor the conduit in place, thereby preventing migration of the conduit after it is placed between the left ventricle and the coronary artery.

Single Loop Conduit

Figure 46A:
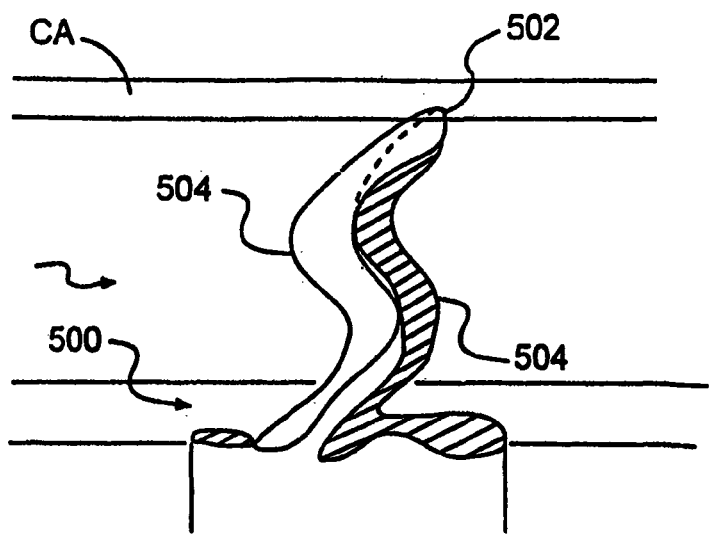
FIG. 46A is a schematic side view of a conduit having a single loop anchoring mechanism.
Figure 46B:
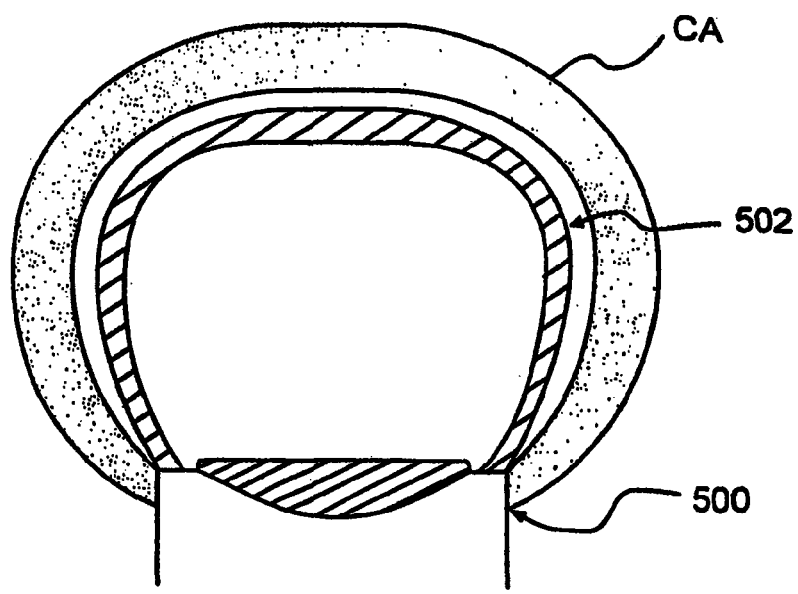
FIG. 46B is a front view of the conduit of FIG. 46A.

FIGS. 46A and 46B illustrate an alternative embodiment of a conduit 500, having a single loop 502 (similar to a basket handle) used to anchor the conduit 500 in the coronary artery CA. The conduit 500 is preferably a one-piece construction formed from a nitinol tube. The loop 502 can be heat formed, such that it conforms to the inner wall of the coronary artery CA. The loop 502 includes flexure regions 504 which provide elasticity. The elasticity allows the conduit 500 to accommodate artery constriction and variation in the internal diameter of the artery. The loop 502 provides axial and radial support to prevent migration of the conduit 500.

Conduit with Rotating Sheath and Deployable Flanges

Figure 47A:
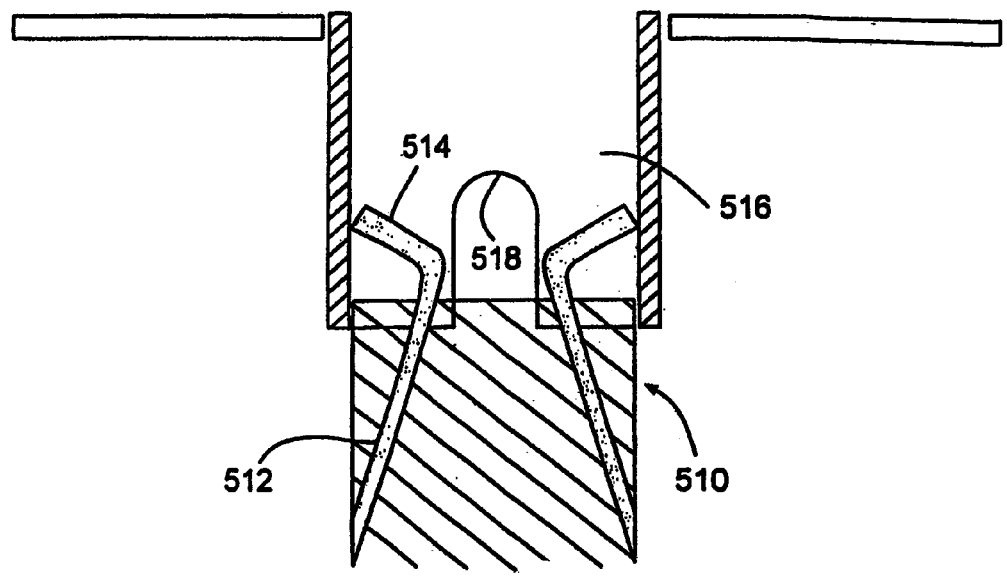
FIG. 47A is a side view of a conduit having deployable flanges.
Figure 47B:
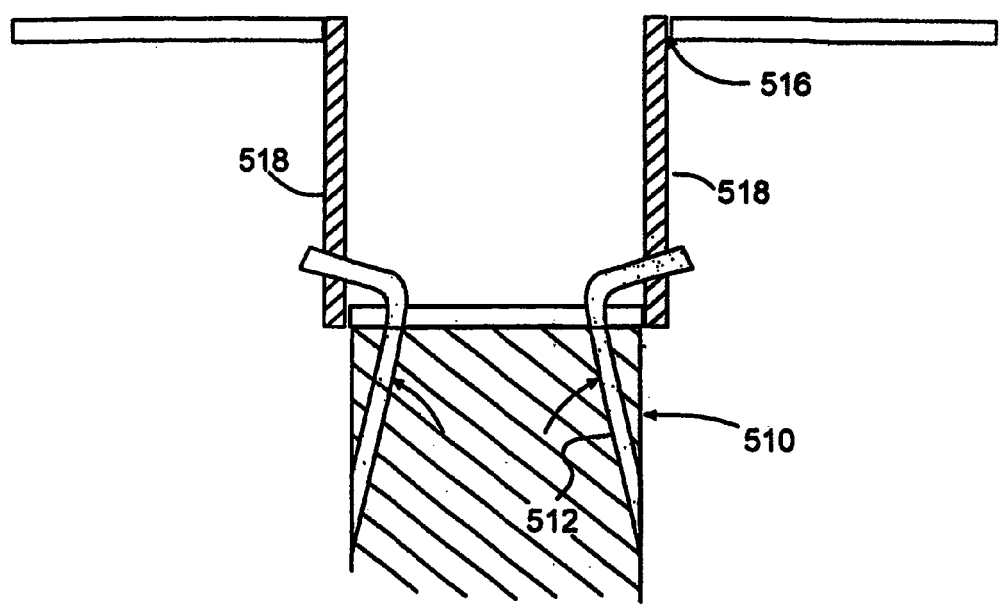
FIG. 47B illustrates the conduit of FIG. 47A with the flanges deployed.

FIGS. 47A and 47B illustrate yet another embodiment of a conduit 510, having deployable flanges 514 used to anchor the conduit 510 in place. The conduit 510 includes a sheath 516 which is rotatable, and flanges 514 that include spring arms 512. The sheath 516 has windows 518 through which the flanges 514 are deployed. Prior to positioning in the body, the sheath 516 is positioned on the conduit 510 so as to retain the flanges 514. After the conduit 510 is properly positioned, the sheath 516 is rotated such that the windows 518 are aligned with the flanges 514. The spring arms 514 cause the flanges 514 to be deployed through the windows 518 following rotation of the retaining sheath 516, thus anchoring the conduit 510 in its proper position. It should be noted that no axial rotation is required to deploy the flanges 514.

It should be appreciated that the stents and conduits described above, and particularly the bulkhead stent, are useful in other applications in addition to stenting the myocardium. For example, these stents may also serve as other types of coronary stents, arterial or venous stents, as well as billiary and esophageal stents.

The present vascular shunt provides significant improvements in the present treatment of blockages in the coronary artery. Although the invention has been described in its preferred embodiments in connection with the particular figures, it is not intended that this description should be limited in any way.

What is claimed is:

1. An implant for providing a passageway of blood between a chamber of the heart and a coronary vessel, comprising:
a conduit body having a first end and a second end and a lumen extending there through and configured to be positioned in a heart wall between a heart chamber and a coronary vessel; and
a top portion connected to one of the first and second ends of the conduit body, the top portion being collapsible into a first configuration and expandable into a second configuration,
wherein the top portion comprises wire loops,
wherein, in the second configuration, the top portion is configured to contact an anterior wall of the coronary vessel and to hold the top portion within the coronary vessel, and
wherein, in the second configuration, the top portion is configured to extend to opposite sides of the conduit body.

2. The implant of claim 1, wherein, in the second configuration, the top portion is configured to extend within the coronary vessel in a direction downstream of the conduit body and in a direction upstream of the conduit body.

3. The implant of claim 1, wherein, in the second configuration, the top portion permits blood flow through the coronary vessel from a position upstream relative to the conduit body to a position downstream relative to the conduit body.

4. The implant of claim 1, wherein the top portion comprises a wire top.

5. The implant of claim 1, wherein the top portion is integrally formed with the conduit body.

6. The implant of claim 1, wherein the conduit body is formed from nickel titanium.

7. The implant of claim 1, wherein the top portion is formed from nickel titanium.

8. The implant of claim 1, further comprising a stainless steel tube connected to the conduit body at an end opposite the top portion.

9. The implant of claim 1, wherein the top portion is formed by laser cutting.

10. The implant of claim 1, wherein the conduit body comprises a solid portion and a mesh portion.

11. The implant of claim 10, wherein the mesh portion is between the solid portion and the top portion.

12. The implant of claim 1, wherein, in the second configuration, the conduit body and the top portion form a substantially T-shaped configuration.

13. The implant of claim 1, further comprising a coating on the conduit body.

14. The implant of claim 1, wherein an end of the conduit opposite the top is configured to pierce tissue.

15. The implant of claim 1, wherein the conduit body has an axially expandable region between the first end and the second end.

16. The implant of claim 1, wherein one of the first end and the second end has a bell shape.

17. The implant of claim 16, wherein the one of the first end and the second end having a bell shape is opposite to the one of the first end and the second end connected to the top portion.

18. The implant of claim 1, wherein the conduit body includes a plurality of fingers configured to extend outward and anchor the conduit body against a wall of the coronary vessel.

19. An implant for providing a passageway of blood between a chamber of the heart and a coronary vessel, comprising:

a conduit body having a first end and a second end and a lumen extending there through and configured to be positioned in a heart wall between a heart chamber and a coronary vessel; and a top portion connected to one of the first and second ends of the conduit body, the top portion being collapsible into a first configuration and expandable into a second configuration, wherein the second configuration is generally ball-shaped, wherein, in the second configuration, the top portion is configured to contact an anterior wall of the coronary vessel and to hold the top portion within the coronary vessel, and wherein, in the second configuration, the top portion is configured to extend to opposite sides of the conduit body.

* * * * *